US006214602B1

(12) United States Patent
Zdanovsky

(10) Patent No.: US 6,214,602 B1
(45) Date of Patent: Apr. 10, 2001

(54) HOST CELLS FOR EXPRESSION OF CLOSTRIDIAL TOXINS AND PROTEINS

(75) Inventor: Alexey G. Zdanovsky, Madison, WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 09/143,634

(22) Filed: Aug. 28, 1998

(51) Int. Cl.$^7$ ............................... C12N 1/20; C12N 5/10
(52) U.S. Cl. ...................................... 435/252.3; 435/325
(58) Field of Search .......................... 435/320.1, 252.3, 435/254.2, 252.33, 325; 536/23.1, 24.3

(56) References Cited

U.S. PATENT DOCUMENTS

| 4,683,195 | 7/1987 | Mullis et al. . |
| 4,683,202 | 7/1987 | Mullis . |
| 4,965,188 | 10/1990 | Mullis et al. . |

FOREIGN PATENT DOCUMENTS

WO 98/08959    4/1999  (WO) .

OTHER PUBLICATIONS

Davis et al, Microbiology, Harper& Row, 1980.*
Schwarz et al, Applied Microbiol & Biotech, 1987, V. 27, No. 1, pp. 50–56, 1987.*
Sun et al, J of Ferm. & Bioeng., V. 84, No. 3, Nov. 1997.*
Websters New World Dictionary, Simon & Schuster, fragment, p. 534, 1988.*
Morbidity and Mortality Weekly Report, Summary of Notifiable Diseases, United States, 1996, 45(53):3 [Oct. 31, 1997].
Anderson and Young, Quantitative Filter Hybridization, in *Nucleic Acid Hybridization* [1985].
Arnon, "Infant Botulism," *Ann. Rev. Med.* 31:541–558 [1980].
Arnon, "Infant Botulism: Epidemiology and Relation to Sudden Death Syndrome," *Epidemiol. Rev.* 3:45–66 [1981].
Arnon et al., "Intestinal Infection and Toxin Production by *Clostridium Botulinum* as One Cause of Sudden Infant Death Syndrome," *Lancet* pp. 1273–1276, Jun. 17, 1978.
Arnon, "Infant Botulism: Anticipating the Second Decade," *J. Infect. Dis.* 154:201–206 [1986].
Balady, "Botulism Antitoxin Fielded for Operation Desert Storm," USAMRDC Newsletter, p. 6 [1991].
Berkow and Fletcher (eds.), "Bacterial Diseases," *Merck Manual of Diagnosis and Therapy,* 16th ed., pp. 116–126, Merck Research Laboratories, Rahway, N.J. [1992].
Boshart et al., "A Very Strong Enhancer Is Located Upstream of an Immediate Early Gene of Human Cytomegalovirus," *Cell* 41:521–530 [1985].
Carruthers et al., "Botulism A exotoxin use in clinical dermatology," *J. Am. Acad. Dermatol.,* 34:788–797 [1996].

Chamberlain et al., "New RNA Polymerase from *Escherichia coli* infected with Bacteriophage T7," *Nature* 228:227–231 [1970].
Dijkema, et al., "Cloning and expression of the chromosomal immune interferon gene of the rate," *EMBO J.* 4:761–767 [1985].
Engelkirk et al. "Classification", *Principles and Practice of Clinical Anaerobic Bacteriology,* pp. 22–23, Star Publishing Co., Belmont, CA [1992].
Frankovich and Arnon, "Clinical Trial of Botulism Immune Globulin for Infant Botulism," *West. J. Med.* 154:103 [1991].
Franz et al., in *Botulinum and Tetanus Neurotoxins,* DasGupta (ed.), Plenum Press, New York [1993], pp. 473–476.
Garcia et al., "The *E. coli* dnaY Gene Encodes an Arginine Transfer RNA," *Cell* 45:453–459 [1986].
Gorman et al., "The Rous sarcoma virus long terminal repeat is a strong promoter when introduced into a variety of eukaryotic cells by DNA–mediated transfection," *Proc. Natl. Acad. Sci. USA* 79:6777–6781 [1982].
Hatheway, "Toxigenic Clostridia," *Clin. Microbiol. Rev.* 3:66–98 [1990].
Holzer, "Botulismus durch Inhalation," *Med. Klin.* 41:1735–1738 [1962].
Kacian et al., "A Replicating RNA Molecule Suitable for a Detailed Analysis of Extracellular Evolution and Replication," *Proc. Natl. Acad. Sci. USA* 69:3038–3042 [1972].
Kim et al., "Use of the human elongation factor 1α promoter as a versatile and efficient expression system," *Gene* 91:217–223 [1990].
Komine et al., "Genomic Organization and Physical Mapping of the Transfer RNA Genes in *Escherichia coli* K12," *J. Mol. Biol.,* 212:579–598 [1990].
Lesley et al., "Use of in vitro Protein Synthesis from Polymerase Chain Reaction–generated Templates to Study Interaction of *Escherichia coli* Transcription Factors with Core RNA Polymerase and for Epitope Mapping of Monoclonal Antibodies," *J. Biol. Chem.,* 266:2632 [1991].
MacDonald et al., "The Changing Epidemiology of Adult Botulism in the United States," *Am. J. Epidemiol.* 124:794–799 [1986].
Makoff et al., "Expression of Tetanus Toxin Fragment C in *E. coli:* Its Purification and Potential Use as a Vaccine," *Bio/Technol.* 7:1043–1046 [1989].

(List continued on next page.)

Primary Examiner—Michael Pak
Assistant Examiner—Sharon L. Turner

(57) ABSTRACT

The present invention is directed to methods and compositions useful in the overproduction of Clostridium toxins and proteins by hosts such as *E. coli*. These proteins and toxins find use in various medical and veterinary applications, including vaccine production, and cosmetic dermatology, as well as treatment of neurological and other diseases and conditions.

6 Claims, 8 Drawing Sheets

OTHER PUBLICATIONS

Makoff et al., "Expression of tetanus toxin fragment C in *E. coli*; high level expression by removing rare codons," *Nucl. Acids Res.* 17:10191–10202 [1989].

Maniatis et al., "Regulation of Inducible and Tissue–Specific Gene Expression," *Science* 236:1237–1245 [1987].

Martin and Kowalchyk, "Docked Secretory Vesicles Undergo $Ca^{2a}$–activated Exocytosis in a Cell–free System," *J. Biol. Chem.*, 272:14447–15543 [1997].

McClung, J., "Human Food Poisoning Due to Growth of *Clostridium Perfringens* (*C. welchii*) in Freshly cooked Chicken: Preliminary Note," *J. Bacteriol.*, 50:229–231 [1945].

Mizushima and Nagata, "pEF–BOS, a powerful mammalian expression vector," *Nuc. Acids. Res.*, 18:5322 [1990].

Nakajima et al., "In Vitro Transcription of the supB–E tRNA Operon of *Escherichia coli*," *J. Biol. Chem.*, 257:11113–11120 [1982].

Nakajima et al., "Organization and Structure of an *E. coli* tRNA operon containing seven tRNA genes," *Cell* 23:239–249 [1981].

Nemoto et al., "*Clostridium botulinum* C3 ADP–ribosyltransferase Gene," *J. Biol. Chem.* 266:19312–19319 [1991].

Perelle et al., "Characterization of *Clostridium perfringens* Iota–Toxin Genes and Expression in *Escherichia coli*," *J. Biol. Chem.*, 61:5147–5156 [1993].

Peterson et al., "The Sudden Infant Death Syndrome and Infant Botulism," *Rev. Infect. Dis.* 1:630–634 [1979].

Sambrook et al., *Molecular Cloning: A Laboratory Manual*, 2nd ed., Cold Spring Harbor Laboratory Press, New York [1989] pp. 16:6–16.8.

Schwarz and Arnon, "Botulism Immune Globulin for Infant Botulism Arrives—One Year and a Gulf War Later," *Western J. Med.* 156:197–198 [1992].

Siegmund and Fraser (eds.), "Clostridial Infections," *Merck Veterinary Manual*, 5th ed., pp. 396–409, Merck & Co., Rahway, NJ. [1979].

Sneath et al., "Clostridium," *Bergey's Manual® of Systemic Bacteriology*, vol. 2, pp. 1141–1200, Williams & Wilkins [1986].

Stephen and Petrowski, "Toxins Which Traverse Membranes and Deregulate Cells," in *Bacterial Toxins*, 2nd ed., pp. 66–67, American Society for Microbiology [1986].

Strickland et al., "Sequence Identity between the $\alpha_2$–Macroglobulin Receptor and Low Density Lipoprotein Receptor–related Protein Suggests That This Molecule Is a Multifunctional Receptor," *J. Biol. Chem.*, 265:17401–17404 [1990].

Strickland et al., "Primary Structure of α2–Macroglobulin Receptor–associated Protein," *J. Biol. Chem.* 266:13364–13369 [1991].

Sugiyama, "*Clostridium botulinum* Neurotoxin," *Microbiol. Rev.* 44:419–448 [1980].

Swartz, "Anaerobic Spore–Forming Bacilli: The Clostridia," pp. 633–646, in Davis et al., (eds.), *Microbiology*, 4th edition, J.B. Lippincott Co. [1990].

Tacket et al., "Equine Antitoxin Use and Other Factors That Predict Outcome in Type A Foodborne Botulism," *Am. J. Med.* 76:794–798 [1984].

Uetsuki, et al., "Isolation and Characterization of the Human Chromosomal Gene for Polypeptide Chain Elongation Factor–1α," *J. Biol. Chem.*, 264:5791–5798 [1989].

Voss, et al., "The role of enhancers in the regulation of cell–type–specific transcriptional control," *Trends Biochem. Sci.*, 11:287–289 [1986].

Wells and Wilkins, "Clostridia: Sporeforming Anaerobic Bacilli," in Baron (ed.), *Medical Microbiology*, 4th ed., University of Texas Medical Branch at Galveston [1991], pp. 261–277.

Wu and Wallace, "The Litigation Amplification Reaction (LAR)—Amplification of Specific DNA Sequences Using Sequential Rounds of Template–Dependent Ligation," *Genomics* 4:560–569 [1989].

Zubay, G., "In Vitro Synthesis of Protein in Microbial Systems," *Ann. Rev. Genet.*, 7:267 [1973].

Clayton et al., "Protective vaccination with a recombinant fragment of *Clostridium botulinum* neurotoxin serotype A expressed from a synthetic gene in *Escherichia coli*," *Infect. Immun.* 63(7):2738–2742 [1995].

Emilsson and Kurland, "Growth rate dependence of transfer RNA abundance in *Escherichia coli*," *EMBO Journal* 9(13):4359–4366 [1990].

Fairweather et al., "Production of biologically active light chain of tetanus toxin in *Escherichia coli*. Evidence for the importance of the C–terminal 16 amino acids for full biological activity," *FEBS Lett* 323(3):218–222 [1993].

Goldman et al., "Consecutive Low–usage Leucine Codons Block Translation Only When Near the 5' End of a Message in *Escherichia coli*," *J. Mol. Biol.* 245:467–473 [1995].

Ivanov et al., "Effect of tandemly repeated AGG triplets on the translation of CAT–mRNA in *E. coli*," *FEBS* 307:173–176 [1992].

Invanov et al., "Unusual Effect of Clusters of Rare Arginine (AGG) Codons on the Expression of Human Interferon α1 Gene in *Escherichia coli*," *Int. J. Biochem. Cell Biol.* 29:659–666 [1997].

Kim et al., "Overexpression of archaeal proteins in *Escherichia coli*," *Biotechnology Letters* 20:207–210 [1998].

LaPenotiere et al., "Expression of a large, nontoxic fragment of botulinum neurotoxin serotype A and its use as an immunogen," *Toxicon* 33(10):1383–1386 [1995].

Makrides, "Strategies for Achieving High–Level Expression of Genes in *Escherichia coli*," *Microbiological Reviews* 60:512–538 [1996].

Rojiani et al., "Relationship between protein synthesis and concentrations of charged and uncharged $tRNA^{Trp}$ in *Escherichia coli*," *Proc. Natl. Acad. Sci. USA* 87:1511–1515 [1990].

Rosenberg et al., "Effects of Consecutive AGG Codons on Translation in *Escherichia coli*, Demonstrated with a Versatile Codon Test System," *Journal of Bacteriology* 175:716–722 [1993].

Saraffova et al., "Comparative Study on the Effect of Signal Peptide Codons and Arginine Codons on the Expression of Human Interferon–α1 Gene in *Escherichia coli*," *Journal of Interferon and Cytokine Research* 16:745–749 [1996].

Willems et al., "Sequence of the gene coding for the neurotoxin of *Clostridium botulinum* type A associated with infant botulism: comparison with other clostridial neurotoxins," *Res. Microbiol.* 144:547–556 [1993].

Zahn, "Overexpression of an mRNA Dependent on Rare Codons Inhibits Protein Synthesis and Cell Growth," *Journal of Bacteriology* 178:2926–2933 [1996].

Brinkman et al., "High–level expression of recombinant genes in *Escherichia coli* is dependent on the availability of the dnaY gene product," *Gene* 85:109–114 [1989]. This reference was made of record by the Examiner in the Office Action dated Apr. 2, 1999, and is not provided herewith.

Chen et al., "Suppression of the negative effect of minor arginine codons on gene expression; preferential usage of minor codons within the first 25 codons of the *Escherichia coli* genes," *Nucleic Acids Research* 18(6):1465–1473 [1990]. This reference was made of record by the Examiner in the Office Action dated Apr. 2, 1999, and is not provided herewith.

Chen and Inouye, "Role of the AGA/AGG codons, the rarest codons in global gene expression in *Escherichia coli*," *Genes & Devel.* 8:2641–2652 [1994]. This reference was made of record by the Examiner in the Office Action dated Apr. 2, 1999, and is not provided herewith.

Clouthier et al., "tRNA$^{Arg}$ (fimU) and Expression of SEF14 and SEF21 in *Salmonella enteritidis*," *J. Bacteriology* 180(4):840–845 [1998]. This reference was made of record by the Examiner in the Office Action dated Apr. 2, 1999, and is not provided herewith.

Davis et al., in *Microbiology*, Third Edition, Harper & Row Publishers, Hagerstown, MD [1980]. This reference was made of record by the Examiner in the Office Action dated Apr. 2, 1999, and is not provided herewith.

Del Tito, Jr. et al., "Effects of a Minor Isoleucyl tRNA on Heterologous Protein Translation in *Escherichia coli*," *Journal of Bacteriology* 177:7086–7091 [1995]. This reference was made of record by the Examiner in the Office Action dated Apr. 2, 1999, and is not provided herewith.

Garcia et al., "The argU Gene Product Enhances Expression of the Recombinant Human α2–Interferon in *Escherichia coli*," *Ann. NY Acad. Sci.* 782:79–86 [1996]. This reference was made of record by the Examiner in the Office Action dated Apr. 2, 1999, and is not provided herewith.

Hua et al., "Enhancement of Expression of Human Granulocyte–Macrophage Colony Stimulating Factor by ArgU Gene Product in *Escherichia coli*," *Biochemistry and Mol. Biol. Intl.* 32(3):537–543 [1994]. This reference was made of record by the Examiner in the Office Action dated Apr. 2, 1999, and is not provided herewith.

Ikemura, "Correlation Between the Abundance of Yeast Transfer RNAs and the Occurance of the Respective Codons in Protein Genes," *J. Mol. Biol.* 158:573–597 [1982]. This reference was made of record by the Examiner in the Office Action dated Apr. 2, 1999, and is not provided herewith.

Jones et al., "Natural Variation of Tyrosyl–rRNA Synthetase and Comparison with Engineered Mutants," *Biochemistry* 25:18887–1891 [1986]. This reference was made of record by the Examiner in the Office action dated Apr. 2, 1999, and is not provided herewith.

Newman et al., "Role of leuX in *Escherichia coli* colonization of the streptomycin–treated mouse large intestine," *Microbial Path.* 17:301–311 [1994]. This reference was made of record by the Examiner in the Office Action dated Apr. 2, 1999, and is not provided herewith.

Newman et al., "Stimulation of *Escherichia coli* F–18Col⁻ Type–1 fimbriae synthesis by leuX," *FEMS Microbiol. Lttrs.* 122:281–287 [1994]. This reference was made of record by the Examiner in the Office Action dated Apr. 2, 1999, and is not provided herewith.

Ritter et al., "tRNA genes and pathogenicity islands: influence of virulence and metabolic properties of uropathogenic *Escherichia coli*," *Mol. Microbiol.* 17(1):109–121 [1995]. This reference was made of record by the Examiner in the Office Action dated Apr. 2, 1999, and is not provided herewith.

Ritter et al., "The Pai–associated leuX specific tRNA5(Leu) affects type 1 fimbriation in pathogenic *Escherichia coli* by control of FimB recombinase expression" *Mol. Microbiol.,* 25(5):871–882 [1997]. This reference was made of record by the Examiner in the Office Action dated Apr. 2, 1999, and is not provided herewith.

Rojiani et al., "Relationship between protein synthesis and concentrations of charged and uncharged tRNA$^{Trp}$ in *Escherichia coli*," *Proc. Natl. Acad. Sci. USA* 87:1511–1515 [1990]. This reference was made of record by the Examiner in the Office action dated Apr. 2, 1999, and is not provided herewith.

Sangare et al., "Nucleotide sequence of a maize mitochondrial tRNA$^{Ser}$ (UGA) gene," *Nucleic Acids Research* 117(19):7979 [1989]. This reference was made of record by the Examiner in the Office Action dated Apr. 2, 1999, and is not provided herewith.

Schenk et al., "Improved High–Level Expression System for Eukaryotic Genes in *Escherichia coli* using T7 RNA Polymerase and Rare $^{Arg}$tRNAs," *BioTechniques* 19(2):196–200 [1995]. This reference was made of record by the Examiner in the Office Action dated Apr. 2, 1999 and is not provided herewith.

Sharp et al., "Codon usage patterns in *Escherichia coli, Bacillus subtilis, Saccharomyces cerevisiae, Schizosaccharomyces pombe, Drosophila melanogaster* and *Homo Sapiens*; a review of the considerable within–species diversity," Nucleic Acids Research 16(17):8207–8211 [1988]. This reference was made of record by the Examiner in the Office Action dated Apr. 2, 1999, and is not provided herewith.

Spanjaard et al., "Frameshift suppression at tandem AGA and AGG codons by cloned tRNA genes: assigning a codon to argU tRNA and T4 tRNA$^{Arg}$," *Nucleic Acids Research* 18(17):5031–5036 [1990]. This reference was made of record by the Examiner in the Office Action dated Apr. 2, 1999, and is not provided herewith.

Ueda et al., "Effect of a rare leucine codon, TTA, on expression of a foreign gene in *Streptomyces lividans*," *Biochimica et Biophysica Acta* 1172:262–266 [1993]. This reference was made of record by the Examiner in the Office Action dated Apr. 2, 1999, and is not provided herewith.

Wakagi et al., "Cloning of the Gene for Inorganic Pyrophosphatase from a Thermoacidophilic Archaeon, Sulfolobus sp. Strain 7, and Overproduction of the Enzyme by Coexpression of tRNA for Arginine Rare Codon," *Biosci. Biotechnol. Biochem.* 62(12):2408–2414 [1998]. This reference was made of record by the Examiner in the Office Action dated Apr. 2, 1999, and is not provided herewith.

Wahab et al., "Effects of tRNA$_1^{Leu}$ overproduction in *Escherichia coli*," *Molecular Microbiology* 7:253–263 [1993]. This reference was made of record by the Examiner in the Office Action dated Apr. 2, 1999, and is not provided herewith.

White et al., "bldA Dependence of Undecylprodigiosin Production on *Streptomyces coelicolor* A3(2) Involves a Pathway–Specific Regulatory Cascade," *J. Bacteriol.* 179(3):627–633 [1997]. This reference was made of record by the Examiner in the Office Action dated Apr. 2, 1999, and is not provided herewith.

Williams et al., "Truncation of Limonene Synthase Preprotein Provides a Fully Active 'Pseudomature' Form of This Monoterpene Cyclase and Reveals the Function of the Amino–Terminal Arginine Pair," *Biochemistry* 37:12213–12220 [1998]. This reference was made of record by the Examiner in the Office Action dated Apr. 2, 1999, and is not provided herewith.

* cited by examiner

| | NAME OF THE PRIMER | SEQUENCE OF THE PRIMER | AMPLIFIED SEQUENCE |
|---|---|---|---|
| SEQ ID NO. 1 | 5'-Ile-tRNA | 5'-AAGCTTTGGATTGCCACACGGAGTTACTTT | ileX |
| SEQ ID NO. 2 | 3'-Ile-tRNA | 5'-GCTTTTGATCTCTGAGAAAAGAAAAAGGCTGAGGATTTCTCGTCAGC | |
| SEQ ID NO. 3 | 5'-Arg-tRNA | 5'-CTTTTCTTTTCTCGAGATCTCGAGGTCGACTTGAAACCCATTGACTCAGCA | argU |
| SEQ ID NO. 4 | 5'-Arg-tRNA | 5'-GCTTTTGATCTCTGAGGTCGACAATTGACTCAGGCGTCCATTATCAGTG | |
| SEQ ID NO. 5 | Leu-5' | 5'-AACACAAAGTCGACAATAATTGACAATTGAATGAACGC | subB-E |
| SEQ ID NO. 6 | Leu-3' | 5'-GTCAACATCGCCGGCCGACATTGAATGAACGC | |
| SEQ ID NO. 7 | BoNT/A-N | 5'-ATAAGAGGATCCGCGATCGAATTCTTATGTCAATTGTTAATAAACAATTTAATT | BoNT/A-L |
| SEQ ID NO. 8 | BoNT/A-LC | 5'-TAICTTCTGAGAATTCTTATGTCGACATCCAATGTTAACTTGATACATAAATC | |
| SEQ ID NO. 9 | BoNT/B-N | 5'-GGATCCGCGGATCCAGTTACATACAGTTACAATAATAATTTTAATT | BoNT/B-L |
| SEQ ID NO. 10 | BoNT/B-LC | 5'-GAATTCTTATGTCGACATACATCACCATCCTGAGCTTTAAC | |
| SEQ ID NO. 11 | BoNT/B-HN | 5'-CCATGGACACATCATCACCATCCACGGGATCCACAAGCTTATGAAGAAAATTAGCAA | BoNT/B-H |
| SEQ ID NO. 12 | BoNT/B-HC | 5'-GAATTCGGATCCTATTATTCAGTCCACCTTCAT | |
| SEQ ID NO. 13 | BoNT/C-N | 5'-GGATCCGCGGATCCAATAACAATTACAACTTAATGTTTTATTATT | BoNT/C-L |
| SEQ ID NO. 14 | BoNT/C-LC | 5'-GAATTCTTATGTCGACTACAAGAATTAATATATCTTTC | |
| SEQ ID NO. 15 | BoNT/C-HN | 5'-GGATCCGTACAAAATAACTTACAGGTACAAAAC | BoNT/C-H |
| SEQ ID NO. 16 | BoNT/C-HC | 5'-AGATCTTATTCACTTACAGGTACAAAAC | |
| SEQ ID NO. 17 | BoNT/E-N | 5'-GGATCCGCGGATCCAAAAATTAATAGTTTAATTATA | BoNT/E-L |
| SEQ ID NO. 18 | BoNT/E-LC | 5'-GATTCTGATCCAAATTTAAATCGACATACATATCCTAGAATTATTACACCAA | |
| SEQ ID NO. 19 | BoNT/E-HN | 5'-GGATCCAAATTTAAATCTGACATACATATCCTAGAATTATTACACCAA | BoNT/E-H |
| SEQ ID NO. 20 | BoNT/E-HC | 5'-AGATCTTATTTTCTTGCCATCCATGTTCTT | |
| SEQ ID NO. 21 | tctLN | 5'-GGAGATGATACATAAGTCTTTTATGTCGACATACATAATTCCTCCTAAATCTGT | TcNT-L |
| SEQ ID NO. 22 | tct-LC | 5'-AAGTTAAATCAAGCTTTTATGTCGACATACATAATTCCTCCTAAATCTGT | |
| SEQ ID NO. 23 | tctCN | 5'-TGCTTTTAGACATATGGATGGATCAGGCCTAGTTT | TcNT-H |
| SEQ ID NO. 24 | tctHC | 5'-TGAACATATCAAGCTTTTTAATCATTGTCCATCC | |
| SEQ ID NO. 25 | iota/IaN | 5'-ATTATATTACGGATCCAGCTTTTATTGAAAGACCAGAAG | iota Ia |
| SEQ ID NO. 26 | iota/IaC | 5'-ATTTATATTATTACTGCAGTTAATTATCAATGTTGCATCCAAAT | |
| SEQ ID NO. 27 | N-C3 | 5'-GGATCCAGGAGGGTTTCTTAAAGGATAAGAAAGTCAATTTATGTTAG | C3 |
| SEQ ID NO. 28 | IC3-C | 5'-AGATCTGAATTCTTAAATATCATTGCTGTAATCATAAT | |

FIG. 1

| PLASMID | CODON USAGE | | | EFFECT OF tRNA GENE AMPLIFICATION ON EXPRESSION | | |
|---|---|---|---|---|---|---|
| | (ATA) | (AGA) | (CTA) | *ileX* (ATA) | *argU* (AGA) | *leuW* (CTA) |
| PETBoNT/A-L22Km | 3.8% (19) | 2.0% (10) | 1.0% (5) | + | - | - |
| pETBoNT/B-L10 | 6.2% (29) | 2.3% (11) | 0.2% (1) | + | + | - |
| pETBoNT/C-L20 | 5.9% (28) | 3.1% (15) | 0.8% (4) | + | + | - |
| pETBoNT/E-L31 | 4.0% (18) | 2.4% (11) | 1.5% (7) | + | +/- | - |
| pETBoNT/B-H18 | 6.4% (57) | 1.9% (17) | 1.0% (9) | + | + | - |
| pETBoNT/C-H14 | 5.0% (48) | 2.5% (24) | 0.9% (9) | + | + | - |
| pETBoNT/E-H10 | 4.4% (40) | 2.2% (20) | 0.3% (3) | + | + | - |
| pTSC3-7 | 2.4% (6) | 3.2% (8) | 0.8% (2) | - | +/- | - |
| pETiota11Km | 5.1% (23) | 1.7% (8) | 0.8% (4) | + | - | - |
| pETTeNT-L12Km | 4.8% (24) | 1.8% (9) | 1.4% (7) | + | - | - |
| pETTcNT-H4Km | 5.7% (53) | 1.8% (17) | 1.1% (11) | + | +/- | - |

FIG. 7

HOST CELLS FOR EXPRESSION OF CLOSTRIDIAL TOXINS AND PROTEINS

FIELD OF THE INVENTION

The present invention relates to the overproduction of Clostridium toxins and proteins by hosts such as E. coli. These proteins and toxins find use in various medical and veterinary applications, including vaccine production, as well as treatment of neurological and other diseases and conditions.

BACKGROUND OF THE INVENTION

The genus Clostridium is comprised of gram-positive, anaerobic, spore-forming bacilli. The natural habitat of these organisms is the environment and the intestinal tracts of humans and other animals. Indeed, clostridia are ubiquitous; they are commonly found in soil, dust, sewage, marine sediments, decaying vegetation, and mud. (See e.g., Sneath et al., "Clostridium," Bergey's *Manual® of Systematic Bacteriology*, Vol. 2, pp. 1141–1200, Williams & Wilkins [1986]). Despite the identification of approximately 100 species of Clostridium, only a small number have been recognized as etiologic agents of medical and veterinary importance. Nonetheless, these species are associated with very serious diseases, including botulism, tetanus, anaerobic cellulitis, gas gangrene, bacteremia, pseudomembranous colitis, and clostridial gastroenteritis. Table 1 lists some of the species of medical and veterinary importance and the diseases with which they are associated. As virtually all of these species have been isolated from fecal samples of apparently healthy persons, some of these isolates may be transient, rather than permanent residents of the colonic flora.

TABLE 1

Clostridium Species Of Medical And Veterinary Importance*

| Species | Disease |
|---|---|
| C. aminovalericum | Bacteriuria (pregnant women) |
| C. argentinese | Infected wounds; Bacteremia; Botulism; Infections of amniotic fluid |
| C. baratii | Infected war wounds; Peritonitis; Infectious processes of the eye, ear and prostate |
| C. beijerinckikii | Infected wounds |
| C. bifermentans | Infected wounds; Abscesses; Gas Gangrene; Bacteremia |
| C. botulinum | Food poisoning; Botulism (wound, food, infant) |
| C. butyricum | Urinary tract, lower respiratory tract, pleural cavity, and abdominal infections; Infected wounds; Abscesses; Bacteremia |
| C. cadaveris | Abscesses; Infected wounds |
| C. carnis | Soft tissue infections; Bacteremia |
| C. chauvoei | Blackleg |
| C. clostridioforme | Abdominal, cervical, scrotal, pleural, and other infections; Septicemia; Peritonitis; Appendicitis |
| C. cochlearium | Isolated from human disease processes, but role in disease unknown. |
| C. difficile | Antimicrobial-associated diarrhea; Pseudomembranous enterocolitis; Bacteremia; Pyogenic infections |
| C. fallax | Soft tissue infections |
| C. ghnoii | Soft tissue infections |
| C. glycolicum | Wound infections; Abscesses; Peritonitis |
| C. hastiforme | Infected war wounds; Bacteremia; Abscesses |
| C. histolyticum | Infected war wounds; Gas gangrene; Gingival plaque isolate |
| C. indolis | Gastrointestinal tract infections |

TABLE 1-continued

Clostridium Species Of Medical And Veterinary Importance*

| Species | Disease |
|---|---|
| C. innocuum | Gastrointestinal tract infections; Empyema |
| C. irregulare | Penile lesions |
| C. leptum | Isolated from human disease processes, but role in disease unknown. |
| C. limosum | Bacteremia; Peritonitis; Pulmonary infections |
| C. malenominatum | Various infectious processes |
| C. novyi | Infected wounds; Gas gangrene; Blackleg, Big head (ovine); Redwater disease (bovine) |
| C. oroticum | Urinary tract infections; Rectal abscesses. |
| C. paraputrificum | Bacteremia; Peritonitis; Infected wounds; Appendicitis |
| C. perfringens | Gas gangrene; Anaerobic cellulitis; Intra-abdominal abscesses; Soft tissue infections; Food poisoning; Necrotizing pneumonia; Empyema; Meningitis; Bacteremia; Uterine Infections; Enteritis necrotans; Lamb dysentery; Struck; Ovine Enterotoxemia; |
| C. putrefaciens | Bacteriuria (Pregnant women with bacteremia) |
| C. putrificum | Abscesses; Infected wounds; Bacteremia |
| C. ramosum | Infections of the abdominal cavity, genital tract, lung, and biliary tract; Bacteremia |
| C. sartagoforme | Isolated from human disease processes, but role in disease unknown. |
| C. septicum | Gas gangrene; Bacteremia; Suppurative infections; Necrotizing enterocolitis; Braxy |
| C. sordellii | Gas gangrene; Wound infections; Penile lesions; Bacteremia; Abscesses; Abdominal and vaginal infections |
| C. sphenoides | Appendicitis; Bacteremia; Bone and soft tissue infections; Intraperitoneal infections; Infected war wounds; Visceral gas gangrene; Renal abscesses |
| C. sporogenes | Gas gangrene; Bacteremia; Endocarditis; central nervous system and pleuropulmonary infections; Penile lesions; Infected war wounds; Other pyogenic infections |
| C. subterminale | Bacteremia; Empyema; Biliary tract, soft tissue and bone infections |
| C. symbiosum | Liver abscesses; Bacteremia; Infections resulting due to bowel flora |
| C. tertium | Gas gangrene; Appendicitis; Brain abscesses; Intestinal tract and soft tissue infections; Infected war wounds; Periodontitis; Bacteremia |
| C. tetani | Tetanus; Infected gums and teeth; Corneal ulcerations; Mastoid and middle ear infections; Intraperitoneal infections; Tetanus neonatorum; Postpartum uterine infections; Soft tissue infections, especially related to trauma (including abrasions and lacerations); Infections related to use of contaminated needles |
| C. thermosaccharolyticum | Isolated from human disease processes, but role in disease unknown. |

*Compiled from Engelkirk et al. "Classification", Principles and Practice of Clinical Anaerobic Bacteriology, pp. 22–23, Star Publishing Co., Belmont, CA (1992);
Stephen and Petrowski, "Toxins Which Traverse Membranes and Deregulate Cells," in Bacterial Toxins, 2d ed., pp. 66–67, American Society for Microbiology (1986);
Berkow and Fletcher (eds.), "Bacterial Diseases," Merck Manual of Diagnosis and Therapy, 16th ed., pp. 116–126, Merck Research Laboratories, Rahway, N.J. (1992);
and Siegmond and Fraser (eds.), "Clostridial Infections," Merck Veterinary Manual, 5th ed., pp. 396–409, Merck & Co., Rahway, N.J. (1979).

In most cases, the pathogenicity of these organisms is related to the release of powerful exotoxins or highly destructive enzymes. Indeed, several species of the genus Clostridium produce toxins and other enzymes of great medical and veterinary significance (Hatheway, Clin. Microbiol. Rev., 3:66–98 [1990]).

Perhaps because of their significance for human and veterinary medicine, much research has been conducted on these toxins, in particular those of *C. botulinum, C. tetani*, and *C. peringens*, although much recent work has also been conducted on *C. difficile*.

C. botulinum

Several strains of *Clostridium botulinum* produce toxins of significance to human and animal health (Hatheway, Clin. Microbiol. Rev., 3:66–98 (1990]). The effects of these toxins range from diarrheal diseases that can cause destruction of the colon, to paralytic effects that can cause death. Neonates and humans and animals in poor health (e.g, those suffering from diseases associated with old age or immunodeficiency diseases) are particularly at risk for developing severe clostridial diseases such as botulism.

*Clostridium botulinum* produces the most poisonous biological toxin known, with a lethal human dose in the nanogram range. Botulinal toxin blocks nerve transmission to the muscles, resulting in flaccid paralysis. When the toxin reaches airway and respiratory muscles, it results in respiratory failure that can cause death (Arnon, J. Infect. Dis., 154:201–206 [1986]).

*C. botulinum* spores are carried by dust and are found on vegetables taken from the soil, on fresh fruits, and on agricultural products such as honey. Under conditions favorable to the organism, the spores germinate to vegetative cells, resulting in the production of the toxin (Arnon, Ann. Rev. Med., 31:541 [1980]).

Botulism disease may be grouped into four types, based on the method of introduction of toxin into the bloodstream. Food-borne botulism results from ingesting improperly preserved and inadequately heated food that contains botulinal toxin (i.e., the toxin is pre-formed prior to ingestion). There were 355 cases of food-borne botulism in the United States between 1976 and 1984 (MacDonald et al., Am. J. Epidemiol., 124:794 [1986]). The death rate due to botulinal toxin has been reported as 12% and can be higher in particular risk groups (Tacket et al., Am. J. Med., 76:794 [1984]). Wound-induced botulism results from *C. botulinum* penetrating traumatized tissue and producing toxin that is absorbed into the bloodstream. Since 1950, thirty cases of wound botulism have been reported (Swartz, "*Anaerobic Spore-Forming Bacilli: The Clostridia*," pp. 633–646, in Davis et al., (eds.), *Microbiology*, 4th edition, J. B. Lippincott Co. [1990]). Inhalation botulism results when the toxin is inhaled. Inhalation botulism has been reported as the result of accidental exposure in the laboratory (Holzer, Med. Klin., 41:1735 [1962]) and is a potential danger if the toxin is used as an agent of biological warfare (Franz et al., in *Botulinum and Tetanus Neurotoxins*, DasGupta (ed.), Plenum Press, New York [1993], pp. 473–476). Infectious infant botulism results from *C. botulinum* colonization of the infant intestine with production of toxin and its absorption into the bloodstream. It is likely that the bacterium gains entry when spores are ingested and subsequently germinate (Arnon, J. Infect. Dis., 154:201 [1986]). There have been 500 cases reported since it was first recognized in 1976 (Swartz, supra.).

Infant botulism strikes infants who are three weeks to eleven months old (greater than 90% of the cases are infants less than six months) (Arnon, J. Infect. Dis., 154:201 [1986]). Clinical symptoms of infant botulism range from mild paralysis, to moderate and severe paralysis requiring hospitalization, to fulminant paralysis, leading to sudden death (Arnon, Epidemiol. Rev., 3:45 [1981]). It is believed that infants are susceptible, due, in large part, to the absence of the fill adult complement of intestinal microflora. The benign microflora present in the adult intestine provide an acidic environment that is not favorable to colonization by *C. botulinum*. In contrast, infants begin life with a sterile intestine which is gradually colonized by microflora. Because of the limited microflora present in early infancy, the intestinal environment is not as acidic, allowing for *C. botulinum* spore germination, growth, and toxin production. In this regard, some adults who have undergone antibiotic therapy which alters intestinal microflora become more susceptible to botulism. An additional factor accounting for infant susceptibility to infectious botulism is the immaturity of the infant immune system.

Infant botulism has been implicated as the cause of mortality in some cases of Sudden Infant Death Syndrome (SIDS, also known as crib death). SIDS is officially recognized as infant death that is sudden and unexpected and that remained unexplained despite complete post-mortem examination. The link of SIDS to infant botulism came when fecal or blood specimens taken at autopsy from SIDS infants were found to contain *C. botulinum* organisms and/or toxin in 3–4% of cases analyzed (Peterson et al., Rev. Infect. Dis., 1:630 [1979]). In contrast, only 1 of 160 healthy infants (0.6%) had *C. botulinum* organisms in the feces and no botulinal toxin (Arnon et al., Lancet, pp. 1273–76, Jun. 17, 1978.)

In developed countries, SIDS is the number one cause of death in children between one month and one year old (Arnon et al., Lancet, pp. 1273–77, Jun. 17, 1978.) More children die from SIDS in the first year than from any other single cause of death in the first fourteen years of life. In the United States, there are 8,000–10,000 SIDS victims annually (Id).

The chief therapy for severe infant botulism is ventilatory assistance using a mechanical respirator and concurrent elimination of toxin and bacteria using cathartics, enemas, and gastric lavage. There were 68 hospitalizations in California for infant botulism in a single year with a total cost of over $4 million for treatment (Frankovich and Arnon, West. J. Med., 154:103 [1991]).

Different strains of *Clostridium botulinum* each produce antigenically distinct toxin designated by the letters A–G. Serotype A toxin has been implicated in 26% of the cases of food botulism; types B, E and F have also been implicated in a smaller percentage of the food botulism cases (Sugiyama, Microbiol. Rev., 44:419 [1980]). Wound botulism has been reportedly caused by only types A or B toxins (Sugiyama, supra). Nearly all cases of infant botulism have been caused by bacteria producing either type A or type B toxin (exceptionally, one New Mexico case was caused by *Clostridium botulinum* producing type F toxin and another by *Clostridium botulinum* producing a type B-type F hybrid) (Arnon, Epidemiol. Rev., 3:45 [1981]). Type C toxin affects waterfowl, cattle, horses and mink. Type D toxin affects cattle, and type E toxin affects both humans and birds.

A trivalent antitoxin derived from horse plasma is commercially available from Connaught Industries Ltd. as a therapy for toxin types A, B, and E. However, the antitoxin has several disadvantages. First, extremely large dosages must be injected intravenously and/or intramuscularly. Second, the antitoxin has serious side effects such as acute anaphylaxis which can lead to death, and serum sickness. Finally, the efficacy of the antitoxin is uncertain and the treatment is costly (Tacket et al., Am. J. Med., 76:794 [1984]).

A heptavalent equine botulinal antitoxin which uses only the F(ab')2 portion of the antibody molecule has been tested by the United States Military (Balady, USAMRDC Newsletter, p. 6 [1991]). This was raised against impure toxoids in those large animals and is not a high titer preparation.

A pentavalent human antitoxin has been collected from immunized human subjects for use as a treatment for infant botulism. The supply of this antitoxin is limited and cannot be expected to meet the needs of all individuals stricken with botulism disease. In addition, collection of human sera must involve screening out HIV and other potentially serious human pathogens (Schwarz and Arnon, Western J. Med., 156:197 [1992]).

Immunization of subjects with toxin preparations has been done in an attempt to induce immunity against botulinal toxins. A C. botulinum vaccine comprising chemically inactivated (i.e., formaldehyde-treated) type A, B, C, D and E toxin is commercially available for human usage. However, this vaccine preparation has several disadvantages. First, the efficacy of this vaccine is variable (in particular, only 78% of recipients produce protective levels of anti-type B antibodies following administration of the primary series). Second, immunization is painful (deep subcutaneous inoculation is required for administration), with adverse reactions being common (moderate to severe local reactions occur in approximately 6% of recipients upon initial injection; this number rises to approximately 11% of individuals who receive booster injections) (Informational Brochure for the Pentavalent (ABCDE) Botulinum Toxoid, Centers for Disease Control). Third, preparation of the vaccine is dangerous as active toxin must be handled by laboratory workers.

What is needed are safe and effective vaccine preparations for administration to those at risk of exposure to C. botulinum toxins. More efficacious methods for treatment of botulism disease are also needed.

C. perfringens

C. perfringens is reported to be the most widely occurring pathogenic bacterium (See, Hatheway, supra, at p. 77). The organism, first described by Welch and Nuttall in 1892, and named Bacillus aerogenes capsulatus, has also been commonly referred to as C. welchii. C. perfringens is commonly isolated from soil samples, as well as the intestinal contents of humans and other animals. Although other Clostridium species are also associated with gas gangrene (e.g., C. novyi, C. septicum, C. histolyticum, C. tertium, C. bifermentans, and C. sporogenes), C. perfringens is the species most commonly involved. These organisms are not highly pathogenic when introduced into healthy tissue, but are associated with rapidly progressive, devastating infections characterized by the accumulation of gas and extensive muscle and tissue necrosis, when introduced in the presence of tissue injury (e.g., damaged muscle). During active multiplication, invasive strains of clostridia produce exotoxins with necrotizing (i.e., cytolytic), hemolytic, and/or lethal properties. In addition, enzymes such as collagenase proteinase, deoxyribonuclease, and hyaluronidase produced by the organisms result in the accumulation of toxic degradation products in the tissues.

C. perfringens produces four major lethal toxins (alpha, beta, epsilon, and iota), upon which the toxin types of the species are based, as well as nine minor toxins (or soluble antigens), that may or may not be involved in the pathogenicity associated with the organism (See, Hatheway, supra, at 77). These minor toxins are delta, theta, kappa, lambda, mu, nu, gamma, eta, and neuraminidase. In addition, some strains produce an enterotoxin that is responsible for C. perfringens food-borne disease. C. perfringens may be divided into "toxin types" designated as A, B, C, D, and E, based on the toxins produced. For example, most strains of toxin type A produce the alpha toxin, but not the other major lethal toxins (i.e., beta, epsilon, and iota); toxin type B organisms produce all of the major lethal toxins with the exception of iota toxin; toxin type C organisms produce alpha and beta major lethal toxins, but not epsilon or iota toxins; toxin type D organisms produce alpha and epsilon toxins, but not beta or iota toxins; and toxin type E organisms produce alpha and iota toxins, but not beta or epsilon toxins.

The alpha toxin is a lecithinase (phospholipase C), while the beta toxin is a necrotizing, trypsin-labile toxin, the epsilon toxin is a permease, trypsin-activatable toxin, and iota toxin is a dermonecrotic, binary, ADP-ribosylating, trypsin-activatable toxin. The delta toxin is a hemolysin, the theta toxin is an oxygen-labile hemolysin, and cytolysin, the kappa toxin is a collagenase and gelatinase, the lambda toxin is a protease, the mu toxin is a hyaluronidase, and the nu toxin is a DNase. The gamma and eta toxins have not been well-characterized and their existence is questionable (See, Hatheway, supra, at p. 77). The neuraminidase is an N-acetylneuraminic acid glycohydrolase, and the enterotoxin is enterotoxic and cytotoxic.

The various toxins are commonly associated with particular diseases. For example, toxin type A organisms are associated with myonecrosis (gas gangrene), food-borne illness, and infectious diarrhea in humans, enterotoxemia of lambs, cattle, goats, horses, dogs, alpacas, and other animals; necrotic enteritis in fowl; equine intestinal clostridiosis; acute gastric dilation in non-human primates, and various other animal species, including humans. Toxin type B organisms are associated with lamb dysentery, ovine and caprine enterotoxemia (particularly in Europe and the Middle East), and guinea pig enterotoxemia. Toxin type C organisms are associated with Darmbrand (Germany), and pig-bel (New Guinea), struck in sheep, lamb and pig enterotoxemia, and necrotic enteritis in fowl. Toxin type D organisms are associated with enterotoxemia of sheep, and pulpy kidney disease in lambs. Toxin type E organisms are associated with calf enterotoxemia, lamb dysentery, guinea pig enterotoxemia, and rabbit "iota" enterotoxemia. While C. perfringens type A strains are commonly isolated from soil samples, and is also readily found in intestinal contents in the absence of disease, type B, C, D, and E strains apparently do not survive in soils (ie., these strains are obligate parasites).

The earliest reported outbreaks of food-bome disease associated with C. perfringens was reported by McClung in 1945 (McClung, J. Bacteriol., 50:229–231 [1945]). C. perfringens food-borne illness is frequent, but because the symptoms are usually mild, it is often not reported. However, between 1970 and 1980, 567 C. perfringens food-borne illness outbreaks were confined in England, and approximately 25 outbreaks are reported annually in the United States (See, Hatheway, supra, at p. 78).

In addition to food-borne illness, evidence for C. perfringens enterotoxin-induced diarrhea in the absence of food has accumulated. Most cases of diarrhea are associated with antimicrobial treatment and elderly patients. Thus, prevention of this disease involves the avoidance of unnecessary antimicrobials and the preferential use of narrow-spectrum antimicrobials (ie., rather than broad-spectrum antimicrobials).

Currently, prompt surgical debridement of contaminated wounds is the most effective means to prevent anaerobic cellulitis and gas gangrene, as antimicrobial therapy alone is insufficient Once a clostridial wound infection has become established, prompt surgical debridement is necessary. In cases of anaerobic cellulitis, wide excision of the affected area and debridement are required, while gas gangrene usually requires complete extirpation of the involved muscle (i.e., usually amputation of the limb is necessitated).

High doses of penicillin are usually administered, although the emergence of penicillin-resistant strains has resulted in the use of clindamycin, chloramphenicol, and metronidazole. However, strains resistant to tetracycline, chloramphenicol, erythromycin, and clindamycin have been observed. Hyperbaric oxygen (3 atm) in a compression chamber is sometimes used, especially in situations where complete debridement is precluded, such as chest infections.

Polyvalent equine antitoxin prepared against toxic filtrates of four species (*C. perfringens, C novyi, C. septicum,* and *C. histolyticum*) has been used in the prophylaxis and treatment of gas gangrene. However, its efficacy was not established and it is no longer available for clinical use (Swartz, supra, at p. 645).

What is needed are compositions and methods suitable for the rapid treatment and prophylaxis of disease due to *C. perfringens*, as well as other clostridial species associated with histotoxic and/or enterotoxic disease.

*C. tetani*

Although tetanus has been recognized since ancient times (e.g., the disease was described by Hippocrates), it was not hypothesized to have an infectious agent as its cause until 1867 (See e.g., Hatheway, supra, at p. 75). The strictly toxigenic disease caused by *C. tetani* is often associated with puncture wounds that do not appear to be serious. The organism is readily isolated from a variety of sources, including soil and the intestinal contents of many animal species (e.g., humans, horses, etc.). Disease results upon the production of toxin by the organism at a site of trauma. The toxin rapidly binds to neural tissue, resulting in the paralysis and spasms characteristic of tetanus. Largely due to the availability of effective toxoids, tetanus is now largely a disease of non-immunized animals, including humans. For example, neonatal tetanus due to contamination of the umbilical stump is very prevalent in some areas of the world. The disease ranges in severity from mild (i.e., good response to drugs and a very low mortality rate) to severe (ie., moderate response to drugs and a 20–40% mortality rate), to very severe (poor response to treatment, and a 50–90% fatality rate). In less developed countries, the mortality rates are approximately 85% for neonatal tetanus, and 50% for other forms of the disease. Neonatal tetanus is almost always severe and is highly fatal. Approximately one half of the cases reported worldwide are neonatal tetanus.

In the U.S., the incidence of tetanus between 1979 and 1986 ranged from between about 60 and 95 cases per year (See, Hatheway, supra, at p. 75); in 1996, there were 36 reported cases (Morbidity and Mortality Weekly Report, Summary of Notifiable Diseases, United States, 1996, 45(53):3, [Oct. 31, 1997]). Worldwide, there are one million cases reported each year (Wells and Wilkins, "Clostridia: Sporeforming Anaerobic Bacilli," in Baron (ed.), *Medical Microbiology*, 4th ed., University of Texas Medical Branch at Galveston [1991], at p. 268). In some countries, tetanus is still one of the ten leading causes of death.

Tetanus is an extremely dramatic disease resulting from the action of the potent neurotoxin (tetanospasmin). The toxin binds to gangliosides in the central nervous system, and blocks inhibitory impulses to the motor neurons, resulting in prolonged muscle spasms of both flexor and extensor muscles. *C. tetani* also produces "tetanolysin," an oxygen-sensitive hemolysis that is finctionally and serologically related to streptolysin O, and the oxygen-sensitive hemolysis of various other organisms, including at least six Clostridium species (See e.g., Hatheway, at p. 76). This toxin lyses a variety of cells, including erythrocytes, polymorphonuclear leukocytes, macrophages, fibroblasts, ascites tumor cells, HeLa cells, and platelets. It has an affinity for cholesterol and related sterols. Although in experimental studies, the toxin has been shown to cause pulmonary edema and death in mice, intravascular hemolysis in rabbits and monkeys, and cardiotoxic effects in monkeys, its role in *C. tetani* infections remains in question (See, Hatheway, at p. 77).

Although the diagnosis of tetanus is relatively easy in advanced cases, successful treatment depends upon early diagnosis before a lethal amount of toxin can become fixed to neural tissue. Thus, patients are usually treated empirically, prior to receiving laboratory data. Tetanus toxoid is used prophylactically to prevent disease. For immunosuppressed patients who may not respond to prophylactic injections of toxoid, human tetanus immunoglobulin given intramuscularly may be used.

Treatment of diagnosed tetanus involves debridement of the wound to remove the organism from the wound site. This debridement occurs after the patient's spasms have been controlled by benzodiazepines. Penicillin or metronidazole is often used to treat the patient, but may not be necessary. However, it has been hypothesized that penicillin may have an adverse effect by acting synergistically with tetanospasmin (Wells and Wilkins, supra, at p. 269–270). Thus, metronidazole is currently recommended. Human tetanus immunoglobulin is also administered intramuscularly. Supportive treatment (e.g., respiratory assistance, nutritional support and intravenous fluids) is often crucial in patient survival. Analgesics that do not cause respiratory depression are also often used (e.g., codeine, meperidine, and morphine). In cases of clean, minor wounds, tetanus toxoid is administered if the patient has not had a booster dose within the past 10 years, although for serious wounds, toxoid is administered if the patient has not had a booster within the past five years.

Summary

In view of the severity and widespread occurrence of clostridial diseases, it is clear that improved methods and compositions to prevent and treat such diseases are needed. Indeed, methods that are suitable for large-scale production of anti-toxin would be useful in various settings, including in less developed countries, where the resources to provide such anti-toxins are limited.

SUMMARY OF THE INVENTION

The present invention provides methods and compositions for the overproduction of Clostridium toxins and proteins by hosts such as *E. coli*. These proteins and toxins find use in various medical and veterinary applications, including vaccine production, and cosmetic dermatology, as well as treatment of neurological and other diseases and conditions.

The present invention provides a host cell containing a recombinant expression vector, wherein the vector encodes transfer RNAs that recognize rare codons and wherein the host cell expresses at least a fragment of at least one clostridial protein. In preferred embodiments, the rare codons are selected from the group consisting of ATA, AGA, CTA, AUA, AGA, and CUA. In some embodiments, the recombinant expression vector further comprises a selectable marker. In various embodiments, the selectable marker is selected from the group consisting of antimicrobial resistance markers, β-galactosidase markers, and metal resistance markers. In still other embodiments, the host cell is *E. coli*. In particularly preferred embodiments, the host cell is a BL21 (λDE3) cell. In yet other embodiments, the host cell is an anaerobic cell, including, but not limited to eubacterial and archaebacterial cells. In further embodiments, the host cell is an eukaryotic cell, including, but not limited to yeast and mammalian cells.

In particularly preferred embodiments, the clostridial protein expressed by the host cell is selected from the group consisting of light chains of botulinal neurotoxins, heavy chains of botulinal neurotoxins, botulinal C3 protein, clostridial iota toxin Ia protein, and light and heavy tetanus toxin chains. In some preferred embodiments, the clostridial protein is expressed at a level such that the clostridial protein ranges from 6 to 35 percent of the total cell protein. In yet other preferred embodiments, the clostridial protein is expressed at a level such that the clostridial protein ranges from 10 to 25 percent of the total cell protein. In further embodiments, the expression of clostridial protein is compared to expression of clostridial protein in the absence of transfer RNAs that recognize rare codons.

The present invention also provides a host cell containing a recombinant expression vector, wherein the vector encodes transfer RNAs that recognize rare codons, wherein the growth of the host cell is uninhibited by the expression of the transfer RNAs. In particularly preferred embodiments, the rare codons are selected from the group consisting of ATA, AGA, CTA, AUA, AGA, and CUA. In some embodiments, the recombinant expression vector further comprises a selectable marker. In various embodiments, the selectable marker is selected from the group consisting of antimicrobial resistance markers, β-galactosidase markers, and metal resistance markers. In alternative embodiments, the host cell is *E coli*. In particularly preferred embodiments, the host cell is a BL21 (λDE3) cell. In yet other embodiments, the host cell is an anaerobic cell, including, but not limited to eubacterial and archaebacterial cells. In still further embodiments, the host cell is an eukaryotic cell, including, but not limited to yeast and mammalian cells.

In particularly preferred embodiments, the clostridial protein expressed by the host cell is selected from the group consisting of light chains of botulinal neurotoxins, heavy chains of botulinal neurotoxins, botulinal C3 protein, clostridial iota toxin Ia protein, and heavy and light tetanus toxin chains. In some preferred embodiments, the clostridial protein is expressed at a level such that the clostridial protein ranges from 6 to 35 percent of the total cell protein. In yet other preferred embodiments, the clostridial protein is expressed at a level such that the clostridial protein ranges from 10 to 25 percent of the total cell protein. In further embodiments, the expression of clostridial protein is compared to expression of clostridial protein in the absence of transfer RNAs that recognize rare codons.

The present invention also provides a host cell containing a recombinant expression vector, the vector encoding transfer RNAs that recognize rare codons, and wherein the recombinant expression vector is selected from the group consisting of pACYC-Ile7, pACYC-Arg34, pACYC-RL5, pACYC-L10, pACYC-IleArg10, pACYC-IRL10, and pACYC-IleArgLeu17. In particularly preferred embodiments, the rare codons recognized by the transfer RNAs are selected from the group consisting of ATA, AGA, CTA, AUA, AGA, and CUA codons. In still other particularly preferred embodiments, the rare codons recognized by the transfer RNAs are selected from the group consisting of ATA, AGA, and CTA codons. In some embodiments, the recombinant expression vector further comprises a selectable marker. In various embodiments, the selectable marker is selected from the group consisting of antimicrobial resistance markers (e.g., β-lactamase) and β-galactosidase markers, and metal resistance markers. In alternative embodiments, the host cell is *E. coli*. In yet other embodiments, the expression vector further comprises an affinity tag. In particularly preferred embodiments, the host cell is a BL21 (λDE3) cell. In further embodiments, the host cell is an anaerobic cell, including but not limited to eubacterial and archaebacterial cells. In yet other embodiments, the host cell is an eukaryotic cell, including, but not limited to yeast and mammalian cells.

In particularly preferred embodiments, the clostridial protein expressed by the host cell is selected from the group consisting of light chains of botulinal neurotoxins, heavy chains of botulinal neurotoxins, botulinal C3 protein, clostridial iota toxin Ia protein, and tetanus toxin. In some preferred embodiments, the clostridial protein is expressed at a level such that the clostridial protein ranges from 6 to 35 percent of the total cell protein. In yet other preferred embodiments, the clostridial protein is expressed at a level such that the clostridial protein ranges from 10 to 25 percent of the total cell protein. In further embodiments, the expression of clostridial protein is compared to expression of clostridial protein in the absence of transfer RNAs that recognize rare codons.

The present invention also provides a host cell capable of expressing a recombinant clostridial protein wherein the clostridial protein is expressed at a level of at least 15% of the total cell protein. In preferred embodiments, the recombinant clostridial protein is expressed at a level of 20 to 35% of the total cell protein. In particularly preferred embodiments, the clostridial protein expressed by the host cell is selected from the group consisting of light chains of botulinal neurotoxins, heavy chains of botulinal neurotoxins, botulinal C3 protein, clostridial iota toxin Ia protein, and heavy and light tetanus toxin chains. In further embodiments, the expression of clostridial protein is compared to expression of clostridial protein in the absence of transfer RNAs that recognize rare codons.

In some embodiments, the recombinant expression vector further comprises a selectable marker. In various embodiments, the selectable marker is selected from the group consisting of antimicrobial resistance markers, β-galactosidase markers, and metal resistance markers. In alternative embodiments, the host cell is *E. coli*. In yet other embodiments, the expression vector further comprises an affinity tag. In particularly preferred embodiments, the host cell is a BL21 (λDE3) cell. In further embodiments, the host cell is an anaerobic cell, including but not limited to eubacterial and archaebacterial cells. In yet other embodiments, the host cell is an eukaryotic cell, including but not limited to yeast and mammalian cells.

The present invention further provides a host cell containing a recombinant expression vector, wherein the vector encodes transfer RNAs that recognize rare codons, wherein the rare codons are selected from the group consisting of ATA, AGA, CTA, AUA, AGA, and CUA, and wherein the expression vector further encodes at least a fragment of at least one clostridial protein. In some embodiments, the recombinant expression vector further comprises a selectable marker. In various embodiments, the selectable marker is selected from the group consisting of antimicrobial resistance markers, β-galactosidase markers, and metal resistance markers. In alternative embodiments, the host cell is *E. coli*. In yet other embodiments, the expression vector further comprises an affinity tag. In particularly preferred embodiments, the host cell is a BL21 (λDE3) cell. In still other embodiments, the host cell is an anaerobic cell, including but not limited to eubacterial and archaebacterial cells. In further embodiments, the host cell is an eukaryotic cell.

In particularly preferred embodiments, the clostridial protein expressed by the host cell is selected from the group consisting of light chains of botulinal neurotoxins, heavy chains of botulinal neurotoxins, botulinal C3 protein, clostridial iota toxin Ia protein, and heavy and light tetanus toxin chains. In some preferred embodiments, the clostridial protein is expressed at a level such that the clostridial protein ranges from 6 to 35 percent of the total cell protein. In yet other preferred embodiments, the clostridial protein is expressed at a level such that the clostridial protein ranges from 10 to 25 percent of the total cell protein. In further embodiments, the expression of clostridial protein is compared to expression of clostridial protein in the absence of transfer RNAs that recognize rare codons.

The expression of clostridial protein(s) by the expression vectors of the present invention may also be used in methods such as in vitro translation systems. For example, it is contemplated that the present invention will find use in prokaryotic as well as eukaryotic systems (e g, TNT® coupled transcription/translation systems [Promega], and *E. coli* T7 S30 systems, etc.). It is not intended that the present invention be limited to any particular expression system or format.

DESCRIPTION OF THE FIGURES

FIG. 1 is a table listing the primers (SEQ ID NOs: 1–28) used during the development of the present invention.

FIG. 7 shows codon usage in recombinant genes and the effect of amplification of tRNA encoding genes on production of clostridial proteins in *E. coli*.

DESCRIPTION OF THE INVETION

Figure 2A:
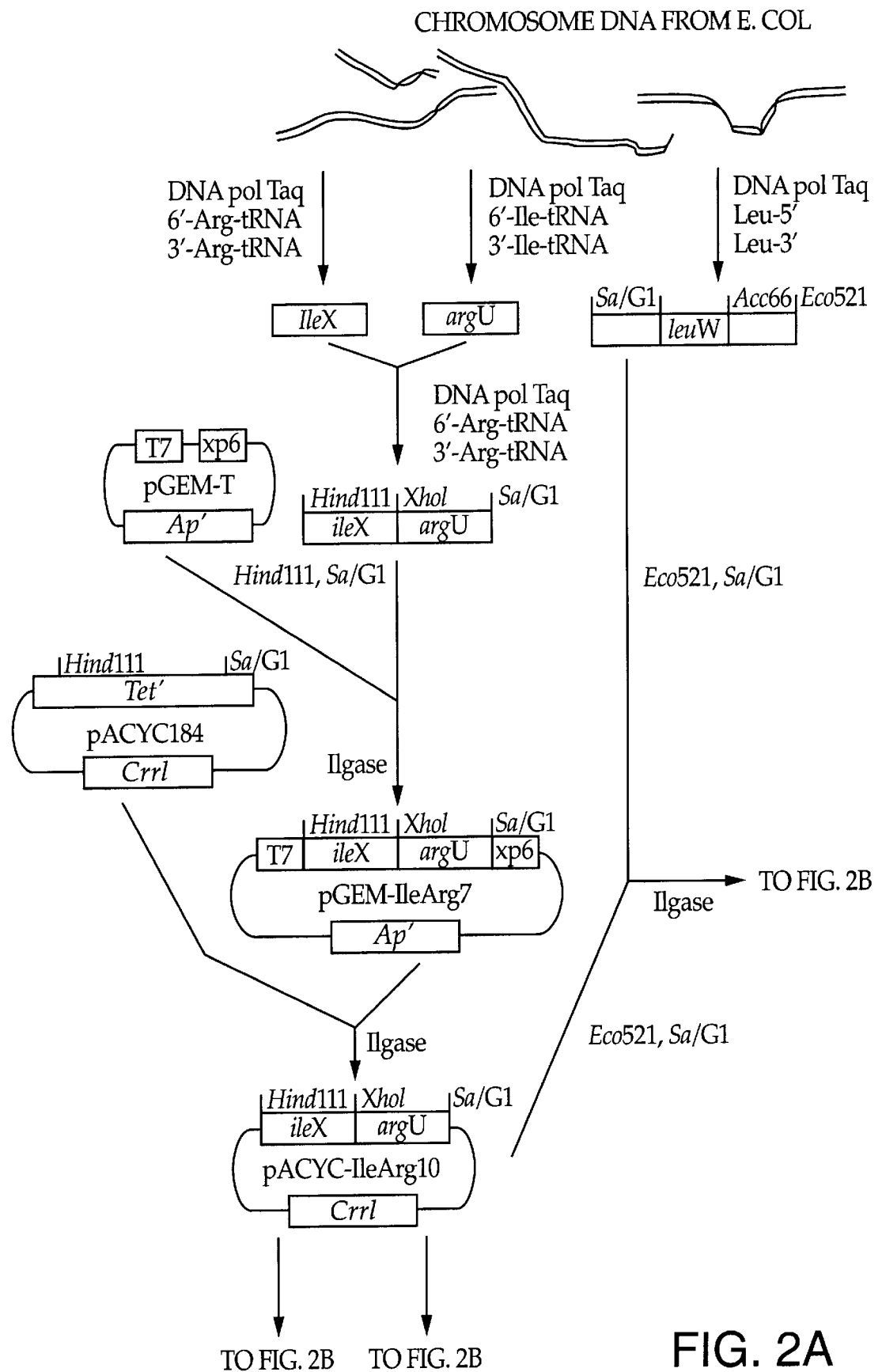
FIG. 2 is a diagram showing the construction of plasmids encoding tRNAs.

The present invention provides methods and compositions for the overproduction of *Clostridium* toxins and proteins by hosts such as *E. coli*. These proteins and toxins find use in various medical and veterinary applications, including vaccine production, and cosmetic dermatology, as well as treatment of neurological and other diseases and conditions.

Clostridial genes are extremely A-T rich and as a consequence contain codons specific for amino acids which are rarely used in *E. coli* (in addition, clostridial genes are difficult to express in yeast as the A-T rich sequences contain signals recognized in yeast as termination signals). To overcome the expression problems caused by clostridial genes in *E. coli*, the present invention provides methods to overexpress the ileX and argU genes which encode cognate tRNAs for rarely used codons in *E. coli* in conjunction with native clostridial gene sequences. The present invention provides methods and compositions to achieve the production of at least 2 times more clostridial protein in *E. coli* cells which co-express the tRNA genes as compared to *E. coli* cells which do not express the tRNA genes. For example, in some embodiments of the present invention, it is possible to obtain clostridial protein expression such that 6–35% of the total cell protein is comprised of clostridial protein.

Previous attempts to express clostridial proteins using native gene sequences in *E. coli* and yeast have proven problematic (See e.g., Makoff et al., Bio/Technol., 7:1043–104 [1989]; and Makoff et al., Nucl. Acids Res., 17:10191–10202 [1989]). The art's approach to this problem typically has been to use synthetic gene sequences which lack the rare codons or premature termination signals found in the native gene (i.e., for expression in *E. coli* and yeast, respectively). In contrast, the present invention provides unexpected advantages in the expression of clostridial proteins. For example, the present invention provides compositions (e.g., plasmid constructs) that contain both the argU and ileX genes which facilitate high levels of expression of the clostridial gene sequences. The present invention further provides useful and novel methods and compositions which successfully and consistently increase expression of clostridial genes in *E. coli* by co-expressing two tRNA genes.

Thus, the present invention provides methods and compositions suitable for the economical and efficient overexpression of clostridial proteins in organisms which do not require an anaerobic environment for growth (e.g., *E. coli*). In this manner, the difficulties associated with growing anaerobes (i.e., Clostridium sp.) are avoided, and routine laboratory methods used to overexpress proteins in recombinant hosts are possible. By providing compositions and methods to overexpress clostridial proteins in facultative anaerobes, the present invention provides methods and compositions which permit the large-scale development of antisera, vaccines (e.g., anti-toxins) and toxoids for the prevention and treatment of disease due to members of the genus Clostridium. In addition, the present invention provides methods and compositions for the production of clostridial toxins suitable for use in the treatment of various neuromuscular and ophthalmological conditions (e.g., strabismus, and blepharospasm), as well as focal distonia and hemifacial spasm, spastic dysphonia, and spasmodic torticolis (See e.g, Hatheway, supra, at p. 74), as well as in clinical dermatology and plastic surgery (See e.g., Carruthers et al., J. Am. Acad. Dermatol., 34:788–797 [1996]).

In addition, the present invention provides methods and compositions for the production of clostridial proteins in cell-free systems. In these methods, the concentrations of tRNAs recognizing rarely used codons (particularly ATA and AGA) are increased. In this embodiment, the present invention provides methods to produce clostridial proteins without relying upon particular host organisms. These systems also facilitate the large-scale development of antisera, vaccines (e.g., anti-toxins) and toxoids for the prevention and treatment of disease due to members of the genus Clostridium, as well as the various therapeutic uses of these toxins.

For example, it is contemplated that cell-free systems in which *E. coli* transformed with plasmids such as pACYC-IleArg10, pACYC-IRL10, etc., carrying genes for tRNAs of interest (e.g., ileX and argu) are used to prepare the cell-free system. Various methods, such as those known in the art may be modified to (See e.g., Zubay, Ann. Rev. Genet., 7:267 [1973]; and Lesley et al., J. Biol. Chem., 266:2632 [1991]) to accomplish this.

It is also contemplated that other methods, such as co-introduction in commercially available cell-free transcription systems (See e.g., *E. coli* S30 Extract Systems, Promega) for the production of two constructs (i.e., plasmids). In this system, one plasmid encodes the protein of interest and the other encodes the tRNA of interest.

DEFINITIONS

To facilitate understanding of the invention, a number of terms are defined below.

The term "gene" refers to a DNA sequence that comprises control and coding sequences necessary for the production of a polypeptide or precursor. The polypeptide can be encoded by a full length coding sequence or by any portion of the coding sequence so long as the desired enzymatic activity and/or antigenic properties are retained.

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product. In some embodiments, the clostridial proteins encoded by "modified" or "mutant" genes are referred to as "non-naturally occurring" clostridial proteins, while the clostridial proteins encoded by the wild-type gene are referred to as "naturally occurring" clostridial proteins.

A clostridial protein is said to be "derived from the genus Clostridium," if that protein comprises all or a portion of the amino acid sequence of the protein sequence produced by a species of Clostridium. Clostridial proteins derived from *C. perfringens* include the native iota toxin obtained from *C. perfringens* cells (Genbank Accession No. D17555), as well as recombinant iota toxin encoded by the wild-type iota toxin gene or mutant iota toxin genes, including but not limited to, genes. Clostridial proteins derived from *C. botulinum* include the native C3 protein and botulinal toxin (e.g, toxins A, B, C, D, E, F, and G), as well as recombinant C3 protein, and recombinant botulinal toxin encoded by the wild-type C3 protein (Genbank Accession No. D17555) and botalinal toxin genes (e.g., type A [Genbank Accession No. X73423], type B [Genbank Accession Nos. X70819, X70814, ZI 1934, and M81186], type C [Genbank Accession No. D49440], type D [Genbank Accession No. X54254], type E [Genbank Accession Nos. X70815, X70818, X62683, and X62089], type F [Genbank Accession Nos. X70821, X70820, X70816, and M92906], and type G [Genbank Accession No. X74162]), or mutant C3 protein or mutant botulinal toxin genes. Clostridial proteins derived from C tetani include the native tetanus toxin, as well as recombinant tetanus toxin encoded by the wild-type tetanus toxin gene (Genbank Accession Nos. X06214 and X04436) or mutant tetanus toxin genes. The term also encompasses clostridial proteins derived from other Clostridium species, including but not limited to *C. argentiensis, C. baratti, C. novyii, C. chauvoei, C. difficile, C. sordelli*, etc.

The term "full-length protein" refers to a protein which encompasses essentially every amino acid encoded by the gene encoding the protein. Those of skill in the art know there are subtle modifications of some proteins in living cells so that the protein is actually a group of closely related proteins with slight alterations. For example, some but not all proteins a) have amino acids removed from the amino-terminus, and/or b) have chemical groups added which could increase molecular weight. Most bacterial proteins as encoded contain a methionine and an alanine residue at the amino-terminus of the protein; one or both of these residues are frequently removed from active forms of the protein in the bacterial cell. These types of modifications are typically heterogenous so not all modifications happen to every molecule. Thus, the natural "full-length" molecule is actually a family of molecules that start from the same amino acid sequence but have small differences in how they are modified. The term "full-length protein" encompasses such a family of molecules.

As used herein, the terms "cell," "cell line," and cell culture" are used interchangeably and all such designations include progeny. The words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

As used herein, the term "vector" is used in reference to nucleic acid molecules that transfer DNA segment(s) from one cell to another. The term "vehicle" is sometimes used interchangeably with "vector."

The terms "recombinant DNA vector" as used herein refers to DNA sequences containing a desired coding sequence and appropriate DNA sequences necessary for the expression of the operably linked coding sequence in a particular host organism. DNA sequences necessary for expression in prokaryotes include a promoter, optionally an operator sequence, a ribosome binding site and possibly other sequences. Eukaryotic cells are known to utilize promoters, polyadenylation signals and enhancers. It is not intended that the term be limited to any particular type of vector. Rather, it is intended that the term encompass vectors that remain autonomous within host cells (e.g., plasmids), as well as vectors that result in the integration of foreign (e.g., recombinant nucleic acid sequences) into the genome of the host cell.

The term "expression vector" and "recombinant expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals. It is contemplated that the present invention encompasses expression vectors that are integrated into host cell genomes, as well as vectors that remain unintegrated into the host genome.

The terms "in operable combination," "in operable order," and "operably linked," as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "transfection" as used herein refers to the introduction of foreign DNA into cells (eukaryotic or prokaryotic). Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementary may be "partial," in which only some of the nucleic acids' bases are matched according to the base pairing rules. Or, there may be "complete" or "total" complementary between the nucleic acids. The degree of complementary between nucleic acid strands has significant effects on the efficiency and strength of hybridization between nucleic acid strands. This is of particular importance in amplification reactions, as well as detection methods which depend upon binding between nucleic acids.

The term "homology" refers to a degree of complementary. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (ie., the hybridization) of one completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

Low stringency conditions comprise conditions equivalent to binding or hybridization at 42° C. in a solution consisting of 5× SSPE (43.8 g/l NaCl, 6.9 g/l NaH$_2$PO$_4$.H$_2$O and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma) and 100 µg/ml denatured salmon sperm DNA] followed by washing in a solution comprising 5× SSPE, 0.1% SDS at 42° C. when a probe of about 500 nucleotides in length is employed.

The art knows well that numerous equivalent conditions may be employed to comprise low stringency conditions; factors such as the length and nature (e.g., DNA, RNA, base composition) of the probe and nature of the target (e.g., DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions which promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described above.

When used in reference to a single-stranded nucleic acid sequence, the term "substantially homologous" refers to any probe which can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

A primer is said to be "capable of hybridizing to a DNA molecule" if that primer is capable of annealing to the DNA molecule; that is the primer shares a degree of complementarity with the DNA molecule. The degree of complementarity may be, but need not be, a complete degree of complementarity (i.e., the primer need not be 100% homologous to the DNA molecule). Indeed, when mutagenic PCR is to be conducted, the primer will contain at least one mismatched base which cannot hybridize to the DNA molecule. Any primer which can anneal to and support primer extension along a template DNA molecule under the reaction conditions employed is capable of hybridizing to a DNA molecule.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (i.e., ELISA, as well as enzyme-based histochemical assays), fluorescent, radioactive, and luminescent systems. It is not intended that the present invention be limited to any particular detection system or label. The terms "reporter molecule" and "label" are used herein interchangeably. Primers and deoxynucleoside triphosphates may contain labels; these labels may comprise, but are not limited to, $^{32}P$, $^{33}P$, $^{35}S$ or fluorescent molecules (e.g., fluorescent dyes).

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195, 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (i.e., hybridization with a labeled probe; incorporation of biotinylated primers followed by avidin-enzyme conjugate detection; incorporation of $^{32}P$-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., *Proc. Natl. Acad. Sci* USA 69:3038 [1972]). Other nucleic acid will not be replicated by this amplification enzyme. Similarly, in the case of T7 RNA polymerase, this amplification enzyme has a stringent specificity for its own promoters (Chamberlin et al., *Nature* 228:227 [1970]). In the case of T4 DNA ligase, the enzyme will not ligate the two oligonucleotides where there is a mismatch between the oligonucleotide substrate and the template at the ligation junction (Wu and Wallace, *Genomics* 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (Erlich (ed.), *PCR Technology*, (Stockton Press [1989]).

As used herein, the terms "PCR product," "PCR fragment," and "amplification product," refer to the resultant mixture of compounds after two or more cycles of the PCR steps of denaturation, annealing and extension are complete.

These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

Transcriptional control signals in eukaryotes comprise "promoter" and "enhancer" elements. Promoters and enhancers consist of short arrays of DNA sequences that interact specifically with cellular proteins involved in transcription (Maniatis et al., *Science* 236:1237 [1987]). Promoter and enhancer elements have been isolated from a variety of eukaryotic sources including genes in yeast, insect and mammalian cells and viruses; analogous control elements (ie., promoters), are also found in prokaryotes. The selection of a particular promoter and enhancer depends on what cell type is to be used to express the protein of interest. Some eukaryotic promoters and enhancers have a broad host range while others are functional in a limited subset of cell types (for review See, Voss, et al., *Trends Biochem. Sci.,* 11:287 [1986], and Maniatis, et al., supra [1987]). For example, the SV40 early gene enhancer is very active in a wide variety of cell types from many mammalian species and has been widely used for the expression of proteins in mammalian cells (Dijkema, et al., *EMBO J.* 4:761 [1985]). Two other examples of promoter/enhancer elements active in a broad range of mammalian cell types are those from the human elongation factor 1α gene (Uetsuki, et al., *J. Biol. Chem.,* 264:5791 [1989], Kim, et al., *Gene* 91:217 [1990], and Mizushima and Nagata, *Nuc. Acids. Res.,* 18:5322 [1990]) and the long terminal repeats of the Rous sarcoma virus (Gorman, et al., *Proc. Natl. Acad Sci.* USA 79:6777 [1982]) and the human cytomegalovirus (Boshart et al., *Cell* 41:521 [1985]).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook et al., *Molecular Cloning: A Laboratory Manual,* 2nd ed., Cold Spring Harbor Laboratory Press, New York [1989] pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is one which is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (Sambrook, supra, at 16.6–16.7).

Eukaryotic expression vectors may also contain "viral replicons" or "viral origins of replication." Viral replicons are viral DNA sequences which allow for the extrachromosomal replication of a vector in a host cell expressing the appropriate replication factors. Vectors which contain either the SV40 or polyoma virus origin of replication replicate to high copy number (up to $10^4$ copies/cell) in cells that express the appropriate viral T antigen. Vectors which contain the replicons from bovine papillomavirus or Epstein-Barr virus replicate extrachromosomally at low copy number (~100 copies/cell).

The clostridial proteins and toxins may be expressed in either prokaryotic or eukaryotic host cells. Nucleic acid encoding the clostridial proteins and toxins may be introduced into bacterial host cells by a number of means including transformation of bacterial cells made competent for transformation by treatment with calcium chloride or by electroporation. If the clostridial proteins or toxins are to be expressed in eukaryotic host cells, nucleic acid encoding the protein or toxin of interest may be introduced into eukaryotic host cells by a number of means including calcium phosphate co-precipitation, spheroplast fusion, electroporation and the like. When the eukaryotic host cell is a yeast cell, transformation may be affected by treatment of the host cells with lithium acetate or by electroporation.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific MRNA sequence encoding a specific protein, are found in the cell as a mixture with numerous other niRNA s which encode a multitude of proteins. However, isolated nucleic acid encoding a clostridial protein or toxin includes, by way of example, such nucleic acid in cells ordinarily expressing a clostridial protein or toxin where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (ie., the oligonucleotide may single-stranded), but may contain both the sense and anti-sense strands (i.e., the oligonucleotide may be double-stranded).

As used herein the term "coding region" when used in reference to structurul gene refers to the nucleotide sequences which encode the amino acids found in the nascent polypeptide as a result of translation of a mRNA molecule. The coding region is bounded on the 5' side by the nucleotide triplet "ATG" which encodes the initiator methionine and on the 3' side by one of the three triplets which specify stop codons (i.e., TAA, TAG, TGA).

As used herein, the term "purified" or "to purify" refers to the removal of contaminants from a sample. For example, recombinant clostridial proteins and toxins are expressed in bacterial host cells and the proteins and toxins are purified by the removal of host cell proteins; the percent of recombinant toxin or protein is thereby increased in the sample.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

The term "native protein" is used herein to indicate a protein isolated from a naturally occurring (i.e., a nonrecombinant) source. Molecular biological techniques may be used to produce a recombinant form of a protein which has identical properties when compared to the native form of the protein.

As used herein the term "portion" when in reference to an amino acid sequence or a protein (as in "a portion of an amino acid sequence") refers to fragments of that protein. The fragments may range in size from four amino acid residues to the entire amino acid sequence minus one amino acid. Particularly preferred fragments of clostridial proteins and toxins retain one or more of the enzymatic activities associated with the wild-type clostridial toxins or proteins, and/or retain their immunogenicity.

As used herein, the term "fusion protein" refers to a chimeric protein containing the protein of interest (i.e., clostridial proteins and/or toxins, and/or fragments thereof) joined to an exogenous protein fragment (the fusion partner which consists of a non-clostridial protein or toxin). The fusion partner may enhance solubility of the clostridial protein as expressed in a host cell, may provide an affinity tag to allow purification of the recombinant fusion protein from the host cell or culture supernatant, or both. If desired, the fusion protein may be removed from the protein of interest (i.e., clostridial protein or toxins, or fragments thereof) by a variety of enzymatic or chemical means known to the art.

EXPERIMENTAL

The following examples are provided in order to demonstrate and further illustrate certain preferred embodiments and aspects of the present invention and are not to be construed as limiting the scope thereof.

In the disclosure which follows, the following abbreviations apply: ° C. (degrees Centigrade); g (gravitational field); vol (volume); w/v (weight to volume); v/v (volume to volume); BSA (bovine serum albumin); fmol (femtomole); DTT (dithiothreitol); DMF (N, N dimethyl fonnamide); DNA (deoxyribonucleic acid); p (plasmid); μl (microliters); ml (milliliters); pg (micrograms); pmoles (picomoles); mg (milligrams); M (molar); mM (milliMolar); μM (microMolar); nm (nanometers); kdal (kilodaltons); OD (optical density); EDTA (ethylene diamine tetra-acetic acid); IPTG (isopropyl-β-D-thiogalactoside); X-gal (5-bromo-4-chloro-3-indolyl-β-D-galactopyranoside); SDS (sodium dodecyl sulfate); Tris (tris(hydroxymethyl)aminomethane); TBE (Tris-Borate-EDTA, i.e., Tris buffer titrated with boric acid rather than HCl and containing EDTA); PBS (phosphate buffered saline); PAGE (polyacrylamide gel electrophoresis); Tween (polyoxyethylene-sorbitan); Boehringer Mannheim or BM (Boehringer Mannheim, Indianapolis, Ind.); Novagen (Novagen, Inc., Madison, Wis.); Promega (Promega Corp., Madison, Wis.); Millipore (Millipore Corp., Bedford, Mass.); Novex (Novex, San Diego, Calif.); and Zymed (Zymed Laboratories, Inc., South San Francisco, Calif.).

Unless otherwise indicated in the following Examples, the restriction enzymes (e.g., Acc65I, BamHI, BglII, Eco52I, EcoICR, EcoRI, HindIII, NcoI, NdeI, SalGI, StuI, and XhoI), as well as T4 DNA polymerase were obtained from Promega, while the RAPID DNA LIGATION KIT AND EXPAND HIGH FIDELITY PCR SYSTEM™ was obtained from Boehringer Mannheim.

In the following Examples, plasmids were propagated in *E. coli* JM109 (ATCC# 53323) grown in Luria-Bertani medium (LB). For recombinant protein expression, plasmids were transformed into *E. coli* BL21(λDE3), as described by Sambrook et al. (Sambrook et al, *Molecular Cloning. A Laboratory Manual*, Cold Spring Harbor Laboratory Press [1989]). Briefly, an overnight culture of BL21(λDE3) cells was diluted 100 times in LB medium and grown under constant aeration at 37° C., until the $OD_{600}$ reached 0.3–0.4. Then, cells were recovered by centrifugation and resuspended in ice-cold transformation buffer (10 mM potassium acetate pH 7.5, 45 mM $MnCl_2$, 10 mM $CaCl_2$, 100 mM KCl, 3 mM hexamminecobalt chloride, 10% glycerol). After 10 minutes of incubation, the cells were again recovered by centrifugation and resuspended in fresh transformation buffer. DNA of interest were added to the competent cells. The mixture was incubated on ice for 30 minutes. The mixtures were then incubated 2 minutes at 42° C., and then transferred to an ice bath again. Upon addition of 1 ml of LB broth, the cells were placed to 37° C. bath and incubated for 30 min. After incubation, the transformed cells were selected on LB-agar plates containing appropriate antibiotics.

EXAMPLE 1

Amplification of *E. coli* ileX and argU Genes and the subB-E tRNA Operon

This Example describes the construction of plasmids that encode tRNA that recognizes the ATA, AGA, and CTA codons rarely used in E. coli. First *E. coli* ileX and argU genes, as well as the subB-E TRNA operon which contains the leuW gene, were amplified by cloning the appropriate sequences into the multicopy plasmid pACYC184. The sequences for these genes were previously identified (See, Garcia et al., Cell 45:453–459 [1986]; Komine et al., J. Mol. Biol., 212:579–598 [1990]; Nakajima et al., Cell 23:239–249 [1981]; and Nakajima et al., J. Biol. Chem. 257:11113–11120 [1982]). The Genbank Accession Numbers were as follows—leuW (J01713), ileX (X52800), argU (M13153) and dnaY(M13353).

PCR was used to amplify the desired fragments from the *E. coli* chromosome. Fragments containing genes ileX and argU were originally amplified as separate DNA fragments using primers 5'-Ile-tRNA (SEQ ID NO:1) and 3'-Ile-tRNA (SEQ ID NO:2) for amplification of ileX; primers 5'-Arg-tRNA (SEQ ID NO:3) and 3'-Arg-tRNA (SEQ ID NO:4) were used for argU. Amplifications of ileX and argU genes were performed using Expand™ High Fidelity PCR System (Boehringer Mannheim). Amplification was performed in volume of 100 µl, which contained 0.5 µl of *E. coli* chromosome DNA, 2 µl of dNTP mixture (10 mM of each DATP, dTTP, dGTP and dCTP), 2 µl of mixture of appropriate primers (15 µM of each primer in the mixture), 10 µl of Expand HF buffer, 10× conc., without $MgCl_2$, 12 µl of 25 mM $MgCl_2$ and 74.5 µl of water. The reaction mixtures were incubated for 3 min at 94° C., and then 0.5 µl of enzyme mix (high fidelity polymerase) were added to each tube. Amplification was performed under following conditions: 3 cycles of 15 sec at 94° C., 30 sec at 58° C., 1 min at 72° C., 18 cycles of 15 sec at 94° C., 30 sec at 65° C., 1 min at 72° C., followed by incubation for 7 min at 72° C.

Following amplification, the fragments (2 µL of each amplification mixture) were combined together and the resulting mixture was amplified using primers 5'-Ile-tRNA (SEQ ID NO:1) and 3'-Arg-tRNA (SEQ ID NO:4). The amplification conditions were the same as described above for amplification of individual fragments. The resulting amplified fragment was cloned into the pGEM-T vector, for ready isolation of recombinant clones with β-galactosidase as a marker using pGEM-T Vector System I (Promega). This was accomplished by mixing of 5 µl of amplified fragment that was purified by means of extraction from agarose after electrophoresis with 1 µl of pGEM-T vector DNA (Promega), using the RAPID DNA LIGATION™ kit (Boehringer Mannheim), with 2 µl water, 2 µl of 5× DNA dilution buffer (from the Boehringer Mannheim kit), 10 minutes of 2× T4 DNA ligation buffer (60 mM Tris-HCl, pH 7.8, 20 mM $MgCl_2$, 20 mM DTT, and 2 mM ATP), and 1 µl of T4 DNA ligase. After incubation at 20° C. for 10 minutes, the ligation mixture was transformed into JM109 cells, and the cells were plated on LB agar containing ampicillin (100 µg/ml), X-Gal and IPTG. The resulting plasmid pGEM-IleArg7 was isolated from the clone that had white color on X-Gal/IPTG medium and was identified through restriction analysis using either PstI or NcoI, and the resulting fragments were separated by electrophoresis in a 0.9% agarose gel. While the original vector plasmid contained single recognition sites for PstI and NcoI, the pGEM-IleArg7 plasmid had two recognition sites for each of these enzymes.

Figure 2B:
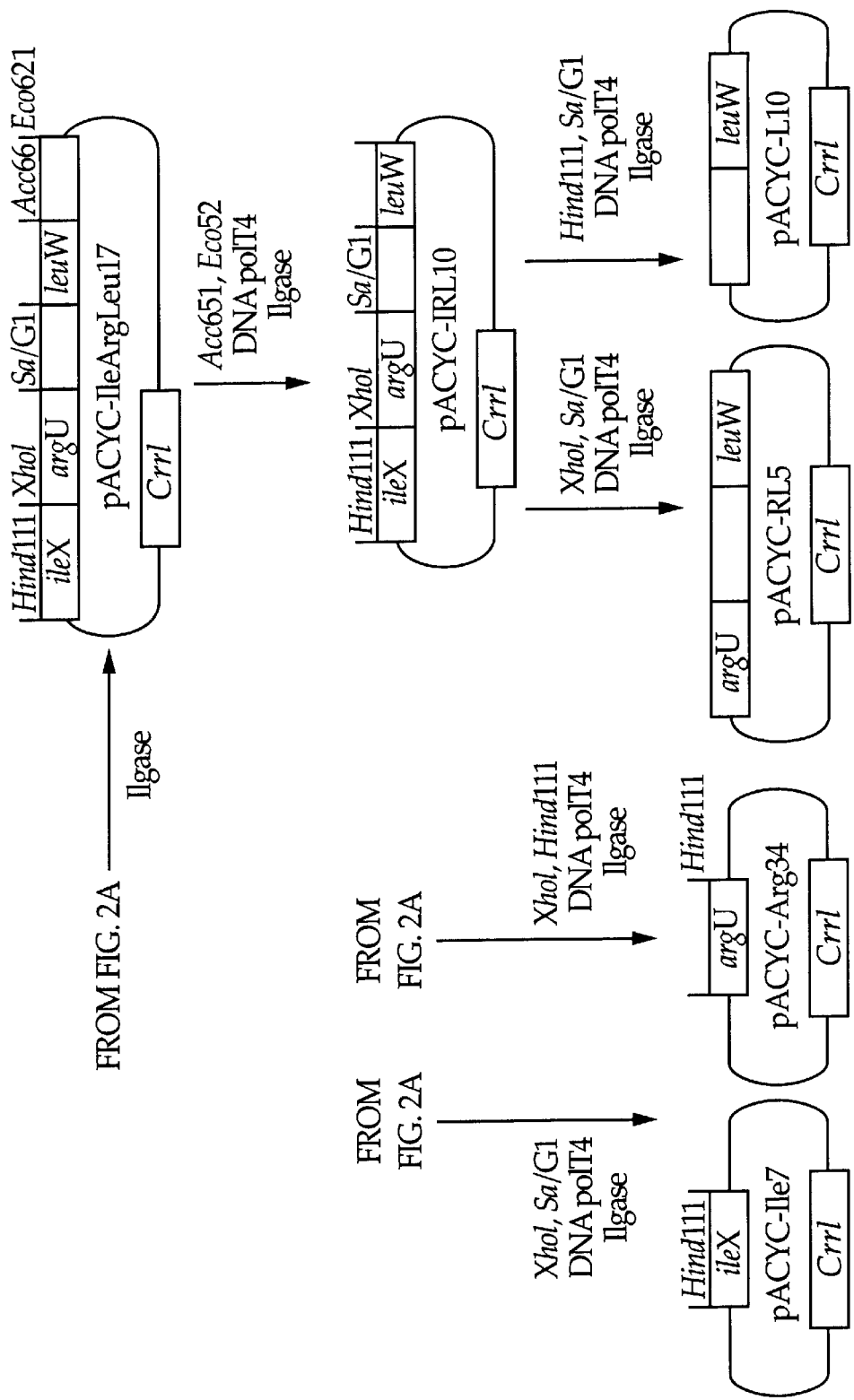

Then, as depicted in FIG. 2, the HindIII-SalGI fragment of plasmid pGEM-IleArg7, containing the ileX and argU genes was joined with the large HindIII-SalGI fragment of plasmid (Promega), to produce plasmid pACYC-IleArg10.

The subB-E TRNA operon was amplified using primers Leu-5' (SEQ ID NO:5) and Leu-3' (SEQ ID NO:6). Amplification was performed using Expand™ High Fidelity PCR System (Boehringer Mannheim). Conditions for amplification were 2 cycles of 10 sec at 96° C., 30 sec at 45° C., 1 min at 72° C., 18 cycles of 10 sec at 96° C., 30 sec at 65° C., 1 min at 72° C. followed by incubation for 7 min at 72° C.

The amplified fragment was treated with SalGI and Eco52I, and then joined with the large EcoRi-SalGI fragment of plasmid pACYC-Ile-Arg10. The resulting plasmid was named pACYC-IleArgLeu17. Upon introduction of this plasmid into *E. coli*, the growth rate of the host cells was substantially decreased. As this decrease was not observed with the parent plasmid pACYC-IleArg10, the entire subB-E tRNA appears to be responsible for this phenotype.

Because the only portion of the subB-E tRNA operon of interest was the leuW gene that is located in the middle of the operon, the 3' terminal part of the subB-E tRNA operon that does not contain leuW gene was removed. This was done by treating the plasmid pACYC-IleArgLeu17 with Eco52I, Acc65I, T4 DNA polymerase and ligase. This was accomplished by incubating 5 µg of pACYC-IleArgLeu7 DNA with 20 units of Eco52I for one hour at 37° C. in 50 µl of 1× Restriction Buffer L (10 mM Tris-HCl, 3 mM MgCl$_2$ and 100 mM NaCl, pH 9.0; Promega). The cleaved DNA was then precipitated with ethanol as known in the art (See e.g., Sambrook et al., *Molecular Cloning: A Laboratory Manual*, Cold Spring Harbor Laboratory Press [1989]), and incubated with Acc65I for one hour at 37° C. in 50 µl 1× Restriction Buffer D (6 mM Tris-HCl, 6 mM MgCl$_2$, 5 mM NaCl, 1 mM DTT, pH 7.9; Promega). After this incubation, the DNA was again precipitated with ethanol, and reconstituted in 24 µl water containing 2 µl Annealing 10× Buffer (Promega) and 3 µl Synthesis 10× Buffer from the Altered Sites II In Vitro Mutagenesis System (Promega), and 1 µl T4 DNA polymerase (1 unit/µl), and incubated for 30 minutes at 37° C. The DNA was again precipitated and reconstituted in 20 µl water. Then, 5 µl of this solution were used in the ligation reaction using the RAPID DNA LIGATION™ kit (Boehringer Manrheim), according to the manufacturer's protocol.

The resulting plasmid was called pACYC-IRL10. It was found that unlike pACYC-IleArgLeu7, this pACYC-IRL10 plasmid did not cause a decrease in host cell growth rate upon its introduction into *E. coli*. These results suggested that the 3' terminal portion of the subB-E tRNA operon was responsible for the inhibition of host cell growth.

In order to determine the influence of each minor tRNA, and the role of each among the three rarely used codons AUA, AGA, and CUA, in the expression of clostridial genes in *E. coli*, plasmids were constructed that encode either the ileX (pACYC-Ile7), or argU (pACYC-Arg34), or leuW (pACYC-L10) genes. Plasmids pACYC-Ile7 and pACYC-Arg34 were derived from pACYC-IleArg10. The first plasmid (pACYC-Ile7) was constructed by subsequent treatment of the parent plasmid with XhoI and SalGI, T4 DNA polymerase, and ligase. This was accomplished by incubating 5 µg of pACYC-Leu7 DNA with 10 units of XhoI and 10 units of SalGI for 1 hour at 37° C. in 50 µl of 1× Restriction Buffer D (Promega) After this incubation, the DNA was precipitated with ethanol, reconstituted in 24 µl of water, mixed with 2 µl of Annealing 10× Buffer and 3 µl of Synthesis 10× Buffer from the Altered Sites II In Vitro Mutagenesis System (Promega) and 1 µl of T4 DNA polymerase (1 unit/µl) and was incubated for 30 min at 37° C. The DNA was precipitated again and reconstituted in 30 µl of water. Then, 5 µl of this solution were used in the ligation reaction using RAPID DNA LIGATION™ Kit (Boehringer Mannheim) according to manufacturer's protocol.

Plasmid pACYC-Arg34 was constructed by subsequent treatment of pACYC-IleArg10 with HindIII and XhoI, T4 DNA polymerase, and ligase. This was accomplished by incubating 5 µg of pACYC-IleArg10 DNA with 10 units of HindIII and 10 units of XhoI for 1 hour at 37° C., in 50 µl of 1× Restriction Buffer B (6 mM Tris-HCl, 6 mM MgCl$_2$, 50 mM NaCl, 1 mM DTT, pH 7.5; Promega). After this incubation, DNA was precipitated with ethanol, reconstituted in 24 µl of water, mixed with 2 µl of Annealing 10× Buffer and 3 µl of Synthesis 10× Buffer from the Altered Sites II In Vitro Mutagenesis System (Promega) and 1 µl of T4 DNA polymerase (1 unit/µl) and was incubated for 30 min at 37° C. The DNA was then precipitated again and reconstituted in 30 µl of water. Then, 5 µl of the solution were used in the ligation reaction using RAPID DNA LIGATION™ Kit (Boehringer Mannheim) according to the manufacturer's instructions.

Plasmid pACYC-L10 was derived from pACYC-IRL10, and was constructed by subsequent treatment of the parent plasmid with SalGI, T4 DNA polymerase, and ligase. To accomplish this, 5 µg of pACYC-IRL10 DNA were incubated with 10 units of SalGI for 1 hour at 37° C. in 50 µl of 1× Restriction Buffer D (Promega). After this incubation, the DNA was precipitated with ethanol, reconstituted in 24 µl of water, mixed with 2 µl of Annealing 10× Buffer and 3 µl of Synthesis 10× Buffer from the Altered Sites II In Vitro Mutagenesis System (Promega) and 1 µl of T4 DNA polymerase (1 unit/µl) and was incubated for 30 min at 37° C. The DNA was precipitated again and reconstituted in 30 µl of water. Then, 5 µl of the solution were used in the ligation reaction using RAPID DNA LIGATION™ Kit (Boehringer Mannheim), according to manufacturer's protocol.

In addition, plasmid pACYC-RL5, which contains argU and leuW was constructed by subsequent treatment of DNA of the plasmid pACYC-IRL10 with HindIII and XhoI, T4 DNA polymerase, and ligase. This was accomplished by incubating 5 µg of pACYC-RL5 DNA with 10 units of HindIII and 10 units of XhoI for 1 hour at 37° C. in 50 µl 1× Restriction Buffer B (Promega). After this incubation, DNA was precipitated with ethanol, reconstituted in 24 µl of water, and mixed with 2 µl of Annealing 10× Buffer and 3 µl of Synthesis 10× Buffer from the Altered Sites II In Vitro Mutagenesis System (Promega) and 1 µl of T4 DNA polymerase (1 unit/µl) and was incubated for 30 min at 37° C. The DNA was precipitated again and reconstituted in 30 µl water. Then, 5 µl of the solution were used in the ligation reaction using RAPID DNA LIGATION™ Kit (Boehringer Mannheim) according to manufacturer's protocol.

EXAMPLE 2

Construction of Plasmids Encoding Botulinal Neurotoxin Fragments

In this Example, plasmids encoding fragments of botulinal neurotoxins were constructed and expressed in *E. coli*.

Fragments of *C. botulinum* DNA encoding light and heavy chains of botulinal toxins B, C, and E were amplified using primers listed in FIG. 1. FIG. 1 indicates the amplified sequences, as well as the primer sequences used for these various experiments. In these experiments, the light chain of botulinal neurotoxin A is often referred to as "BoNT/A," while botinulinal neurotoxins B, C, and E are often referred to as "BoNT/B," "BoNT/C," and "BoNT/E," respectively. DNA from *C. botulinum* strains producing toxins of interest were provided by Dr. Vertiev (Gamalea Institute of Epidemiology and Microbiology, Russia).

PCR was performed using Expand™ High Fidelity PCR System (Boehringer Mannheim) as described above. DNA fragments encoding botulinum toxin light chains were amplified using following cycling protocol: 2 cycles of 15 sec at 94° C., 30 sec at 50° C., 1,5 min at 72° C., 23 cycles of 15 sec at 94° C., 30 sec at 68° C., 1,5 min at 72° C., followed by incubation for 7 min at 72° C. DNA fragments encoding toxin heavy chains were amplified using following cycling protocol: 3 cycles of 15 sec at 94° C., 30 sec at 45° C., 3 min at 72° C., 22 cycles of 15 sec at 94° C., 30 sec at 60° C., 3 min at 72° C. followed by incubation for 7 min at 72° C. Originally, these fragments were cloned into pGEM-T, as described above.

The resulting plasmids encoding light chains of botulinal neurotoxin B, C, and E, were named "pGEM-BoNT/B-L5," "pGEM-BoNT/C-L2," and "pGEM-BoNT/E-L13," respectively. Plasmids encoding heavy chains of botulinal neurotoxin B, C, and E, were named "pGEM-BoNT/B-H13," "pGEM-BoNT/C-H6," and "pGEM-BoNT/E-H10," respectively. Then, BamHI-EcoRI fragments of plasmids pGEM-BoNT/B-L5, pGEM-BoNT/C-L-2, and pGEM-BoNT/E-L13, encoding light chains of botulinal neurotoxins were used to substitute the small BamHI-EcoRI fragment in plasmid pETA32-22, resulting in plasmids pETBoNT/B-L10, pETBoNT/C-L20, and pETBoNT/E-L31, respectively.

Plasmids encoding the light chain of botulinal neurotoxin A (BoNT/A), as well as heavy chains of botinulinal neurotoxins B, C, and E (BoNT/B, C, and E, respectively), were constructed using the plasmid pET28b(+)(Novagen). Plasmid pETBoNT/A-L22m, which encodes the light chain of BoNT/A was constructed by direct substitution of the small BamHI-EcoRI fragment in plasmid pET28b(+) with the fragment amplified from C. botulinum using primers BoNT/A-N (SEQ ID NO:7) and BoNT/A-LC (SEQ ID NO:8). To accomplish this, 10 µg of pET28b(+) DNA were incubated with 20 units of BamHI and 20 units of EcoRI for 1 hour at 37° C. in 100 ml of 1× MULTI-CORE Restriction Buffer (25 mM Tris-Acetate, 10 mM magnesium acetate, 100 mM potassium acetate, 1 mM DTT, pH 7.8; Promega). Similarly, the amplified PCR fragment of C. botulinum DNA encoding light chain of BoNT/A was treated with BamHII and EcoRI. After treatment with restriction endonucleases, the DNA fragments were separated by electrophoresis in 0.9% agarose gel and fragments of interest were isolated as known in the art (See e.g., Sambrook et al., *Molecular Cloning: A Laboratory Manual*, Cold Spring Harbor Laboratory Press [1989]). Isolated fragments were precipitated with ethanol and reconstituted in 20 µl of water. Then, 2.5 µl of each fragment were mixed in the ligation reaction using RAPID DNA LIGATION™ Kit (Boehringer Mannheim) according to the manufacturer's protocol.

Plasmid pETBoNT/B-H18 was constructed by replacement of the NcoI-EcoRI fragment of plasmid pET28b(+) with the small NcoI-EcoRI fragment from pGEM-BoNT/B-H13, as described above. Plasmiids pETBoNT/C-H14 and pETBoNE/E-H10 were generated by subcloning into BamHI site of pET28b(+) the small BamHI-BglII fragments from plasmids pGEM-BoNT/C-H6 and pGEM-BoNT/E-H10, respectively.

These plasmids were propagated in JM109 cells in LB medium containing ampicillin (100 µg/ml) and were used as a stock for plasmid. To analyze the expression of genes encoded by these plasmids, the plasmids isolated from JM109 cells were introduced into E. coli BL21(λDE3) cells. At the same time, these cells were co-transformed with either pACYC184 or its derivatives that encode tRNAs recognizing the rarely used codons "AUA," AGA," and "CUA." For this purpose, competent BL21(λDE3) cells were incubated with two plasmids at the same time. Cells containing both plasmids were selected on LB medium containing either ampicillin (100 µg/ml) and chloramphenicol (10 µg/ml), or kanamycin (30 µg/ml) and chloramphenicol (10 µg/ml). The combination of antibiotics used was based on the combination of plasmids used for co-transformation.

Once the cell density reached an absorbance of 0.5–0.6 at 590 nm, protein expression was induced by the addition of 1 µl of 20% solution of IPTG per 1 ml of culture. After 90 minutes of incubation, the cells were harvested by centrifugation. Light chains of neurotoxins B and E were recovered after dissolving inclusion bodies in buffer containing 6 M guanidine hydrochloride and renaturation in 10 mM Tris-HCl, 1 mM EDTA, 300 mM arginine, pH 7.0. After renaturation by dilution of protein dissolved in 6 M guanidine hydrochloride (10 mg/ml) in 100 volumes of renaturation buffer (10 mM Tris-HCl, 1 mM EDTA, 300 mM arginine, pH 7.5), and incubation of the solution for 24 hours at 4° C. The proteins were then dialyzed against buffer containing 20 mM TrisHCl, 100 mM urea and 1 mM EDTA, pH 7.5. The proteins were then incubated with Q Sepharose (Promega) and the material that did not bind with Q Sepharose was concentrated using ultrafiltration with an Ultrafree-15 PBTK 30,000 NMWL centrifugal Filtration Device (Millipore), according to the manufacturer's protocol.

Figure 3:
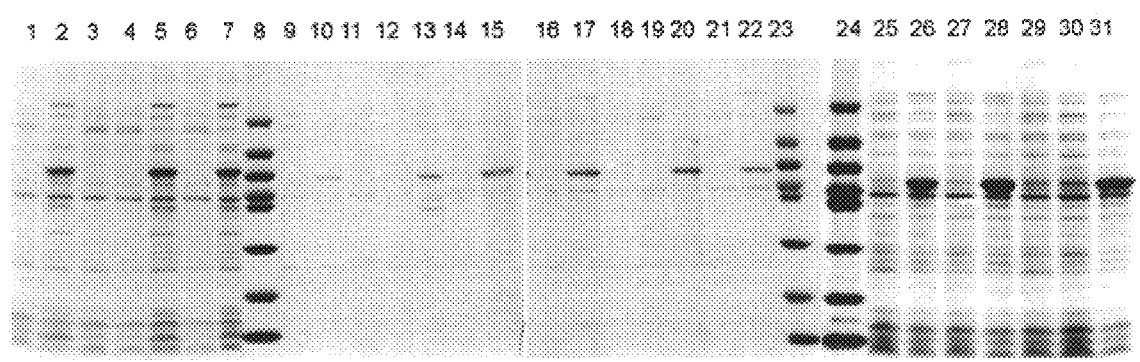
FIG. 3 is a gel showing the effect of amplification of ileX, argU, and leuW genes on the production of botulinal neurotoxin light chains in *E. coli*.
Figure 4:
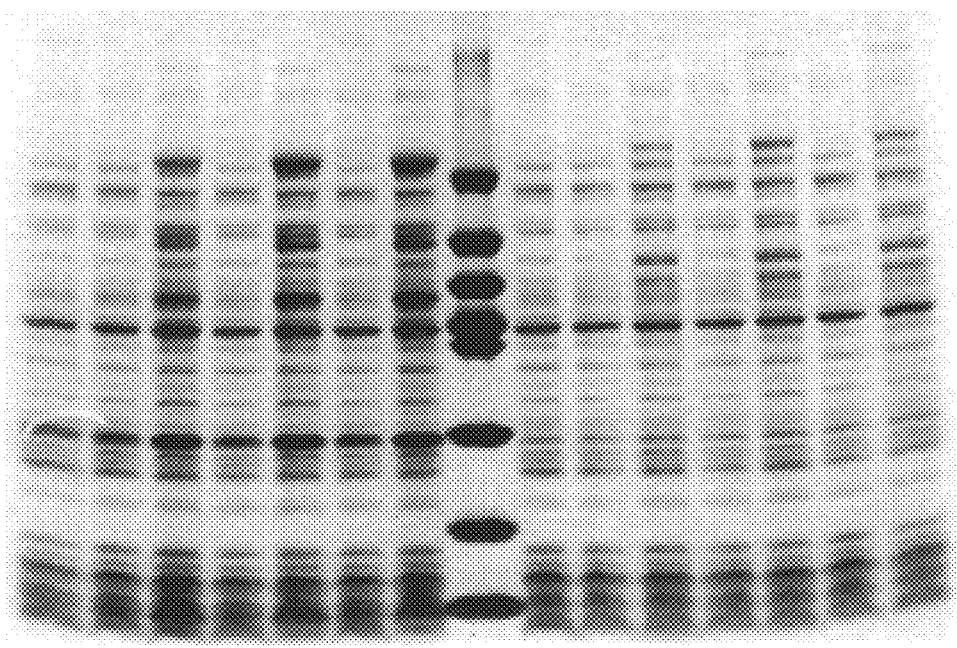
FIG. 4 is a gel showing the effect of amplification of ileX, argU, and leuW genes on the production of botulinal neurotoxin heavy chains in *E. coli*.

FIGS. 3 and 4 are 4–20% SDS-PAGE gels (Novex) that show that cells containing plasmids encoding botulinal fragments and pACYC 184 did not produce any significant amount of protein of interest. In FIG. 3, lanes 1, 9, 16, and 25 contained pACYC-184, while lanes 2, 10, 17, and 26 contained pACYC-Ile7, lanes 3, 11, 18, and 27 contained pACYC-Arg34, lanes 4,12, 19, and 29 contained pACYC-L10, lanes 6, 14, 21, and 30 contained pACYC-RL5, lanes 5, 13, 20, and 28 contained pACYC-IleArg10, and lanes 7, 15, 22, and 31 contained pACYC-IRL10. Also, in this Figure, lanes 1–7 contained pETBoNT/A-L22Km, lanes 9–15 contained pETBoNT/B-L10, lanes 16–22 contained pETBoNT/C-L20, and lanes 25–31 contained pETBoNT/E-L31. Lanes 8, 23, and 24 contained mid-range protein molecular weight markers (Promega).

In FIG. 4, lanes 1 and 9 contained pACYC184, lanes 2 and 10 contained pACYC-Arg34, lanes 3 and 11 contained pACYC-Ile7, lanes 4 and 12 contained pACYC-L10, lanes 5 and 13 contained pACYC-IleArg10, lanes 6 and 14 contained pACYC-RL5, and lanes 7 and 15 contained pACYC-IRL10. Also, lanes 1–7 contained pETBoNT/B-H18, and lanes 8–15 contained pETBoNT/E-H10. Lane 8 contained mid-range protein molecular weight markers (Promega).

As indicated in FIGS. 3 and 4, there also was no significant improvement in production of botulinal neurotoxin fragments in the cells containing pACYC-Arg34, pACYC-L10, or pACYC-RL15. However, production of botulinal neurotoxins was greatly improved in cells containing pACYC-Ile7, pACYC-IleArg10, and pACYC-IRL10.

Immunoassays were used to confimn the identities of expressed proteins. To confirm their identities, the expressed proteins were separated using a 4–20% SDS-PAGE gel (Novex) and transferred using Xcell II Mini-Cell Blot Module (Novex) from the gel onto Immobilon-$P^S$ transfer membrane (Millipore). Proteins were visualized by subsequent incubation of filters with: 1) polyclonal antibodies against specific neurotoxins provided by Dr. Vertiev (Russia); and 2) components of the Immunoblot SP kit for rabbit antibody (Zymed). The identity of the light chains of the botulinal neurotoxins were also confirmed using an enzymatic activity test. In these enzymatic activity tests, the recombinant proteins "synaptobrevin 2-RAP" and "SNAP25-RAP" were used. These proteins contain a soluble portion of rat synaptobrevin 2 (amino acid residues 1–96; Genbank Accession No. Q64357) and complete sequence of rat SNAP25, accordingly, joined with Receptor Associated Protein (Genbank Accession No. P30533; Strickland et al., J. Biol. Chem., 265:17401–17404 [1990]; and Strickland et al., J. Biol. Chem., 266:13364–13369 [1991]).

To detect enzymatic activities, neurotoxin light chains were incubated with the appropriate protein (i.e., synaptobrevin 2 fused with RAP was used as a substrate for the neurotoxin B light chain, while rat SNAP25 fused with RAP was used for the neurotoxin E light chain), in a buffer containing 10 mM Tris-HCl, pH 6.8, and 1 mM $ZnSO_4$ for two hours. To prevent aggregation of synaptobrevin 2-RAP, the reaction mixture also contained heparin (1.25 mg/ml). After incubation, the proteins were separated using a 4–20% SDS-PAGE gel (Novex), and visualized by staining with the colloidal Coomassie Staining kit (Novex), according to the manufacturer's instructions.

Figure 5:
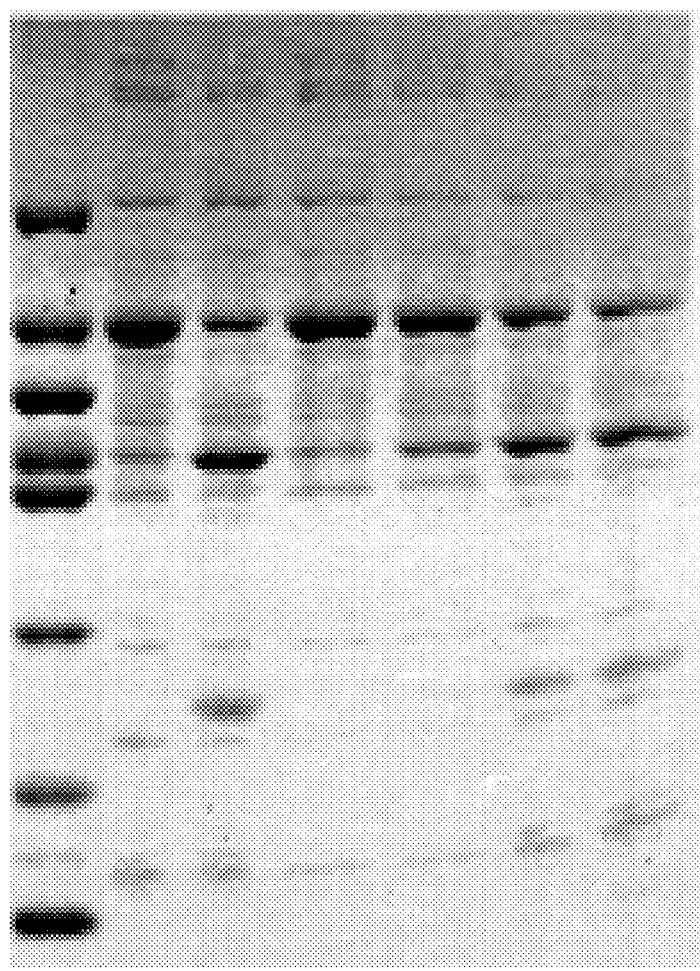
FIG. 5 is a gel showing the cleavage of SNAP25-RAP with recombinant light chain of botulinal neurotoxin E.

The results indicated that the recombinant neurotoxin B light chain, and the recombinant neurotoxin E light chain were enzymatically active. In addition, it was determined that these reactions were inhibited by the use of EDTA (i.e., in agreement with the previously reported ability of EDTA to inhibit enzymatic activity of botulinum toxins), as shown in the 4–20% SDS-PAGE gel (Novex) of FIG. 5. In this Figure, lanes 2 and 4 contained SNAP25-RAP alone, while lanes 3, 5, 6, and 7 contained SNAP25-RAP as well as the light chain of BoNT/E. No EDTA was present in lanes 2, and 3, (i.e.,the buffer used in this experiment contained 10 mM Tris-HCl, pH 6.8), while 100 mM EDTA was included in lanes 4 and 5, 10 mM EDTA was used in lane 6, and 1 mM EDTA was used in lane 7. Lane 1 contained mid-range protein molecular weight markers (Promega).

The recombinant neurotoxin E light chain was also found to be active in inhibiting $Ca^{2+}$-activated exocytosis from LDCV (large dense core vehicle)-plasma membrane complex as described by Martin and Kowalchyk (Martin and Kowalchyk, J. Biol. Chem., 272:14447–15543 [1997]).

EXAMPLE 3

Expression of Other Clostridial Protein

In these experiments, expression plasmids encoding the botulinal C3 protein (Nemoto et al., J. Biol. Chem., 266:19312–19319 [1991]), iota toxin Ia protein from *C. perfringens* (Perelle et al., J. Biol. Chem., 61:5147–5156 [1993]), and tetanus toxin fragments were constructed. Sequences of interest were amplified from total DNA preparations obtained from *C. botulinum*, *C. perfringens*, and *C tetani*, respectively, using PCR and the primers listed in FIG. 1. As indicated above, FIG. 1 indicates the sequences amplified, as well as the primers.

Total DNA from microorganisms producing toxins of interest was provided by Dr. Vertiev (Russia). Amplifications were performed using Expand™ High Fidelity PCR System (Boehringer Mannheim). Each 100 µl of reaction mixture contained 0.5 µl of chromosome DNA, 2 µl of DNTP mixture (10 mM of each dATP, dTTP, dGTP and dCTP), 2 µl of mixture of appropriate primers (15 µM of each primer in the mixture), 10 µl of Expand BF buffer (10× conc.; without $MgCl_2$), 16 µl of 25 mM $MgCl_2$ and 68.5 µl of water. The reaction mixtures were incubated for 3 min at 94° C., and then 0.5 µl of Enzyme mix (high fidelity) were added to each tube. Amplification of fragment encoding botulinum C3 protein was performed under following conditions: 3 cycles of 15 sec at 94° C., 30 sec at 48° C., 1 min at 72° C., 22 cycles of 15 sec at 94° C., 30 sec at 65° C., 1 min at 72° C. followed by incubation for 7 min at 72° C. Amplification of fragment encoding light chain of tetanus toxin was performed under following conditions: 2 cycles of 15 sec at 96° C., 30 sec at 55° C., 1 min 10 sec at 72° C., 28 cycles of 15 sec at 96° C., 30 sec at 65° C., 1 min 10 sec at 72° C., followed by incubation for 7 min at 72° C.

Amplification of fragment encoding heavy chain of tetanus toxin was performed under following conditions: 2 cycles of 15 sec at 96° C., 30 sec at 50° C., 3 min at 72° C., 28 cycles of 15 sec at 96° C., 30 sec at 65° C., and 3 min at 72° C., followed by incubation for 7 min at 72° C. Amplification of fragment encoding Ia domain of iota toxin was performed under following conditions: 2 cycles of 20 sec at 96° C., 30 sec at 50° C., 1 min 10 sec at 72° C., 23 cycles of 20 sec at 96° C., 30 sec at 60° C., 1 min at 72° C. followed by incubation for 7 min at 72° C.

DNA fragment from C. botulinum-encoding C3 was cloned into pGEM-T, as described above. Then, the resulting plasmid (pGEM-C3-20) was subsequently treated with NdeI, DNA polymerase T4, and BglII. This was accomplished by incubating 10 pg of pGEM-C3-20 DNA with 20 units of NdeI for 1 hour at 37° C. in 100 µl of 1× Restriction Buffer D (Promega). After this incubation DNA was precipitated with ethanol, reconstituted in 24 µl water, mixed with 2 µl of Annealing 10× Buffer and 3 µl of Synthesis 10× Buffer from the Altered Sites II In Vitro Mutagenesis System (Promega) and 1 µl of T4 DNA polymerase (1 unit/µl), and was incubated for 30 min at 37° C. The DNA was precipitated again and reconstituted in 100 µl of 1× Restriction Buffer D containing 20 units of BglII. After treatment, fragments of DNA were separated by electrophoresis in 0.9% agarose gel and the small fragment was isolated using methods known in the art (See eg, Sambrook et al., supra).

Similarily, pPhe23-1 was subsequently treated with HindIII, DNA polymerase T4, and BamHI and the large fragment was isolated from 0.9% agarose gel. Treatment with HindIII was performed in 1× Restriction Buffer B (Promega), while treatment with BamHI was performed in 1× Restriction Buffer E (6 mM Tris-HCl, 6 mM $MgCl_2$, 100 mM NaCl, 1 mM DTT, pH 7.5; Promega). Both isolated fragments were joined using RAPID DNA LIGATION™ kit (Boehringer Mannheim) according to the manufactprer's protocol.

The resulting plasmid pTSC3-7 encoded C3 protein. The identity of this protein was confirmed by Western blot analysis. To visualize protein in these Westerns, rabbit anti-C3 antibodies provided by Dr. Vertiev (Russia) were used. For these Westerns, total cell extracts were separated using 4–20% SDS-PAGE gels (Novex), and proteins were transferred onto Immobilon-$P^{SQ}$ membrane (Millipore) using Xcell II Blot Module (Novex) according to manufacturer's protocol. After blocking with 5% BSA and 0.1% Tween 20 in PBS membrane was incubated with anti-C3 antibodies. Bound antibodies were detected with Immunoblot SP kit for rabbit antibody (Zymed). A protein band corresponding to a protein with molecular mass close to the expected 27.4 kDa was detected.

Plasmid pETiota11Km was generated by substitution of a small BamHI-XhoI fragment of plasmid pETSynB53Km with a fragment that was amplified using specific primers form *C. perfringens* DNA (see above), and treated with BamHI and XhoI. To accomplish this, 10 µg of pETSynB53Km DNA were incubated with 20 units of BamHI and 20 units of XhoI for 1 hour at 37° C. in 100 µl of 1× Restriction Buffer B (Promega). Similarly, the amplified by PCR fragment of *C. perfringens* DNA was treated with BamHI and XhoI. After treatment with restriction endonucleases, fragments of DNAs were separated by electrophoresis in 0.9% agarose gel and fragments of interest were isolated using methods known in the art (See e.g., Sambrook et al., supra). Isolated fragments were precipitated with ethanol and reconstituted in 20 µl water. Then, 2.5 µl of each fragment were mixed in the ligation reaction using RAPID DNA LIGATION™ kit (Boehringer Mannheim) according to manufacturer's protocol.

Plasmids encoding light and heavy chains of tetanus toxin were generated by direct cloning of fragments amplified from *C. tetani* DNA into the expression vector pET28b(+). The fragment encoding the light chain of tetanus toxin produced by amplification was treated with NdeI and HindIII, and joined with the big NdeI-HindIII fragment of plasmid pET28b(+). The fragment encoding the heavy chain of tetanus toxin produced by amplification was treated with StuI and HindIII, and joined with the large HindIII-EcoICR fragment of plasmid pET28b(+). To accomplish this, 10 µg of pET28b(+) DNA were incubated with 20 units of HindIII and 20 units of EcoICR for 1 hour at 37° C. in 100 μl of 1× Restriction Buffer B (Promega). Similarly, the PCR-amplified of *C. tetani* DNA was treated with HindII and StuI. After treatment with restriction endonucleases fragments of DNAs were separated by electrophoresis in 0.9% agarose gel and fragments of interest were isolated as known in the art (See e.g. Sambrook et al., supra). Isolated fragments were precipitated with ethanol and reconstituted in 20 μl water. Then, 2.5 μl of each fragment were mixed in the ligation reaction using the RAPID DNA LIGATION™ kit (Boehringer Mannheim) according to manufacturer's instructions. The recombinant plasmids generated were named "pETTeNT-L12Km" and "pETTeNT-H4Km," and encode light and heavy chains of tetanus toxin, respectively.

Figure 6:
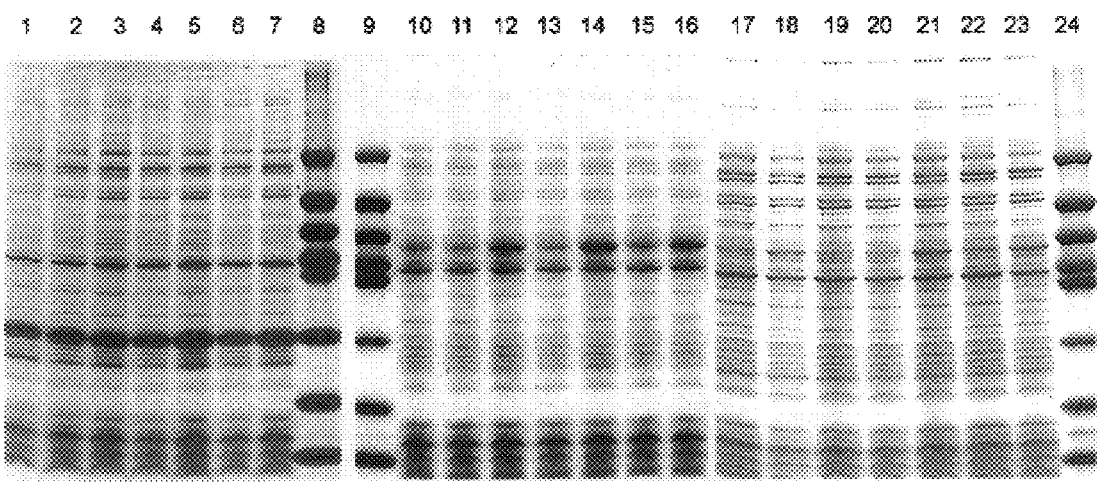
FIG. 6 is a gel showing the effect of amplification of ilex, argU, and leuW genes on the production of botulinal C3 protein, iota toxin Ia protein, and fragments of tetanus toxin by *E. coli*.

The results shown in FIG. 6 demonstrate that plasmids pTSC3-7, pETiota11Km, pETTeNT-L12Km, and pETTeNT-H4Km, unlike the plasmids encoding fragments of botulinal neurotoxins, provide efficient production of recombinant proteins in *E. coli* that contain normal quantities of tRNA genes. However, it was found that improvement of recombinant C3 protein production was not possible by amplifying ileX, argU, and/or leuW genes in *E. coli*. Nonetheless, in the case of the pETiota11K, pETTeNT-L12Km, and pETTeNT-H4Km plasmids, increased production of iota toxin Ia protein, and tetanus toxin fragments was possible by amplification of ileX (See, FIG. 6).

In FIG. 6, lanes 1, 10, and 17 contained pACYC184, lanes 2, 11, and 19 contained pACYC-Arg34, lanes 3, 12, and 18 contained pACYC-Ile7, lanes 4, 13, and 20 contained pACYC-L10, lanes 5, 14, and 21 contained pACYC-IleArg10, lanes 6, 15, and 22 contained pACYC-RL5, and lanes 7, 16, and 23 contained pACYC-IRL10. In addition, lanes 1–7 contained pTSC3-7, lanes 10–16 contained pETiota11Km, and lanes 17–23 contained pETTeNT-L12Km. Lanes 8, 9, and 24 contained mid-range protein molecular weight markers (Promega). As with the previous gels, FIG. 6 shows a 4–20% SDS-PAGE gel (Novex). Also as in previous gels, the proteins were stained using the Coomassie Staining kit (Novex).

FIG. 7 shows the codon usage in recombinant genes and the effect of amplification of tRNA encoding genes on the production of clostridial proteins in *E. coli*. In this Figure, the numbers in parentheses indicate the number of particular codons present in genes of interest in each of the plasmids (ie., for BoNT/A-L in pETBoNT/A-L22Km, there are 19 ATA codons, 20 AGA codons, and 5 CTA codons), while the numbers in the columns indicate the percentages of each codon present (i.e.,for pETBoNTA-L22Km, 3.8% of the codons are ATA, 2.0% of the codons are AGA, and 1.0% of the codons are CTA). Although an understanding of the mechanisms involved is not necessary in order to use the present invention, the results obtained in this Example, as well as the previous Examples indicate that there is a correlation between the frequencies in which the rarely used codons AUA, AGA, and CUA, the effect of amplification of particular TRNA encoding sequences, and the accumulation of particular derivatives of clostridial proteins.

It is clear from the above that the present invention provides compositions and methods for the production of clostridial proteins. Indeed, from the above it is clear that the present invention provides compositions and methods suitable for the preparation of effective multivalent vaccines, antitoxins, and toxoids against various clostridial toxins, as well as preparations suitable for use in the treatment of various neurological conditions and clinical dermatology.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A host cell containing a recombinant expression vector, said vector encoding transfer RNAs that recognize ATA, AGA, and CTA codons, and wherein said recombinant expression vector is selected from the group consisting of pACYC-RL5, pACYC-L10, pACYC-IRL10, and pACYC-IleArgLeu17.

2. The host cell of claim 1, wherein said host cell is capable of expressing at least fragments of at least one clostridial protein.

3. The host cell of claim 2, wherein said clostridial proteins are selected from the group consisting of light chains of botulinal neurotoxins, heavy chains of botulinal neurotoxins, botulinal C3 protein, clostridial iota toxin Ia protein, and light and heavy chains of tetanus toxin.

4. The host cell of claim 2, wherein said clostridial protein is expressed at a level such that the clostridial protein ranges from 6 to 35 percent of the total cell protein.

5. The host cell of claim 2, wherein said clostridial protein is expressed at a level such that the clostridial protein ranges from 10 to 25 percent of the total cell protein.

6. The recombinant expression vector of claim 2, wherein said vector further comprises an affinity tag.

* * * * *

SEQUENCE LISTING

<160> NUMBER OF SEQ ID NOS: 28

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 1
aagctttgga ttgcgacacg gagttacttt                                    30

<210> SEQ ID NO 2
<211> LENGTH: 48
<212> TYPE: DNA
<213> ORGANISM: Artificial Sequence
<220> FEATURE:
<223> OTHER INFORMATION: Description of Artificial Sequence: Synthetic

<400> SEQUENCE: 2
gcttttgatc tctcgagaaa agaaaaaggc tgacgatttc tcgtcagc                48

```
<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: Synthetic

<400> SEQUENCE: 3
cttttctttt tctcgagaga tcaaaagcca ttgactcagc a                    41

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence: Synthetic

<400> SEQUENCE: 4
gcttttgatc tctcgaggtc gactcaggcg tcccattatc agtg                 44

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic

<400> SEQUENCE: 5
aacacaaagt cgacaataat tgacgaatat agcgcc                          36

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic

<400> SEQUENCE: 6
gtcaacatcg cggccgacat tgaatgaacg c                               31

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence: Synthetic

<400> SEQUENCE: 7
ataagaggat ccgcggatgc aatttgttaa taaacaattt aatt                 44

<210> SEQ ID NO 8
<211> LENGTH: 55
<212> TYPE: DNA
<213> ORGANISM: Artificial Sequence
<220> FEATURE:
<223> OTHER INFORMATION: Description of Artificial Sequence: Synthetic

<400> SEQUENCE: 8
tatcttctga gaattcttat gtcgacatcc aattgttaac tttgatacat aaatc     55

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: Synthetic
```

<400> SEQUENCE: 9
ggatccgcgg atgccagtta caataaataa ttttaatt                                38

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: Synthetic

<400> SEQUENCE: 10
gaattcttat gtcgacatac atattcctgg agctttaac                               39

<210> SEQ ID NO 11
<211> LENGTH: 58
<212> TYPE: DNA
<213> ORGANISM: Artificial Sequence
<220> FEATURE:
<223> OTHER INFORMATION: Description of Artificial Sequence: Synthetic

<400> SEQUENCE: 11
ccatgggaca tcatcaccat caccacgggg atccacaagc ttatgaagaa attagcaa          58

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 12
gaattcggat cctattattc agtccaccct tcat                                    34

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence: Synthetic

<400> SEQUENCE: 13
ggatccgcgg atgccaataa caattaacaa ctttaattat t                            41

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: Synthetic

<400> SEQUENCE: 14
gaattcttat gtcgacctac aatctaatgt tttattata                               39

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic

<400> SEQUENCE: 15
ggatcctgta caaaatagga aaatatatct ttc                                     33

<210> SEQ ID NO 16
<211> LENGTH: 29

```
<212> TYPE: DNA
<213> ORGANISM: Artificial Sequence
<220> FEATURE:
<223> OTHER INFORMATION: Description of Artificial Sequence: Synthetic

<400> SEQUENCE: 16
agatcttatt cacttacagg tacaaaacc                                    29

<210> SEQ ID NO 17
<211> LENGTH: 38
<212> TYPE: DNA
<213> ORGANISM: Artificial Sequence
<220> FEATURE:
<223> OTHER INFORMATION: Description of Artificial Sequence: Synthetic

<400> SEQUENCE: 17
ggatccgcgg atgccaaaaa ttaatagttt taattata                          38

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Synthetic

<400> SEQUENCE: 18
gaattcttat gtcgacatac atattgattt ccttatgcc                         39

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence: Synthetic

<400> SEQUENCE: 19
ggatccaaat ttaaatccta gaattattac accaa                             35

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: Synthetic

<400> SEQUENCE: 20
agatcttatt tttcttgcca tccatgttct t                                 31

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Synthetic

<400> SEQUENCE: 21
ggagatgata catatgccaa taaccataaa taatt                             35

<210> SEQ ID NO 22
<211> LENGTH: 52
<212> TYPE: DNA
<213> ORGANISM: Artificial Sequence
<220> FEATURE:
<223> OTHER INFORMATION: Description of Artificial Sequence: Synthetic
```

<400> SEQUENCE: 22
aagttaaatc aagcttttat gtcgacatac ataattctcc tcctaaatct gt        52

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence: Synthetic

<400> SEQUENCE: 23
tgcttttaga catatggatg gatcaggcct agttt        35

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence: Synthetic

<400> SEQUENCE: 24
tgaacatatc aagctttta atcatttgtc catcc        35

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence: Synthetic

<400> SEQUENCE: 25
attatattac ggatccagct tttattgaaa gaccagaag        39

<210> SEQ ID NO 26
<211> LENGTH: 43
<212> TYPE: DNA
<213> ORGANISM: Artificial Sequence
<220> FEATURE:
<223> OTHER INFORMATION: Description of Artificial Sequence: Synthetic

<400> SEQUENCE: 26
atttatatta ctcgagttaa tttatcaatg ttgcatccaa aat        43

<210> SEQ ID NO 27
<211> LENGTH: 52
<212> TYPE: DNA
<213> ORGANISM: Artificial Sequence
<220> FEATURE:
<223> OTHER INFORMATION: Description of Artificial Sequence: Synthetic

<400> SEQUENCE: 27
ggatccagga ggggttttat gaaagggata agaaagtcaa ttttatgttt ag        52

<210> SEQ ID NO 28
<211> LENGTH: 38
<212> TYPE: DNA
<213> ORGANISM: Artificial Sequence
<220> FEATURE:
<223> OTHER INFORMATION: Description of Artificial Sequence: Synthetic

<400> SEQUENCE: 28
agatctgaat tcttaaatat cattgctgta atcataat        38